US006936707B2

(12) United States Patent
Okuda et al.

(10) Patent No.: US 6,936,707 B2
(45) Date of Patent: Aug. 30, 2005

(54) MODIFIED DNA MOLECULE, RECOMBINANT CONTAINING THE SAME, AND USES THEREOF

(75) Inventors: Takashi Okuda, Kawasaki (JP); Shuji Saito, Kawasaki (JP); Kristi M. Moore, Lenexa, KS (US); Yoshinari Tsuzaki, Lenexa, KS (US)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 09/901,572

(22) Filed: Jul. 11, 2001

(65) Prior Publication Data

US 2003/0165534 A1 Sep. 4, 2003

(51) Int. Cl.$^{7}$ ........................ C07H 21/00; A61K 39/02; C12N 15/11; C12N 15/31; C12N 15/79

(52) U.S. Cl. .................. 536/23.7; 536/23.1; 435/320.1; 424/184.1; 424/192.1; 424/196.11; 424/197.11; 424/264.1

(58) Field of Search ........................... 424/184.1, 185.1, 424/187.1, 190.1, 192.1, 199.1; 435/69.1, 69.3, 69.7, 69.8, 70.1, 71.1, 455, 456, 233.1, 239, 320.1, 325; 536/23.1, 23.4, 23.5, 23.7, 23.72

(56) References Cited

U.S. PATENT DOCUMENTS

| | | | | |
|---|---|---|---|---|
| 5,484,970 A | | 1/1996 | Suzuki et al. | |
| 5,489,430 A | | 2/1996 | Saito et al. | |
| 5,656,485 A | * | 8/1997 | Jacobson et al. | 435/252.3 |
| 5,871,742 A | | 2/1999 | Saitoh et al. | |
| 6,103,238 A | | 8/2000 | Essex et al. | |

FOREIGN PATENT DOCUMENTS

| | | |
|---|---|---|
| EP | 0 345 021 A2 | 12/1989 |
| EP | 0 905 140 A1 | 3/1999 |

OTHER PUBLICATIONS

Nahri et al., Protein Engineering, vol. 14 No 2, pp. 135–140 (Jan. 2001).*

Nahri et al., Journal of Biological Chemistry, vol. 266 No 34, pp. 23022–23026 (Dec. 1996).*

Lai et al., Journal of Biological Chemistry, vol. 261 No 7, pp. 3116–3121 (1986).*

Sytkowski et al., Journal of Biological Chemistry, vol. 260 No 27, pp. 14727–14731 (1985).*

Marini et al., Molecular Microbiology, vol. 38 No 3, pp. 552–564 (Nov. 2000).*

Parekh, R., Current Opinion in Biotechnology, vol. 2, pp. 730–734 (1991).*

Yoshida Shigeto et al.; "Identification and Expression of a Mycoplasma Gallisepticum Surface Antigen Recognized by a Monoclonal Antibody Capable of inhibiting Both Growth and Metabolism." Infection and Immunity; vol. 68, No. 6, Jun. 2000, pp. 3186–3192.

Liu Yuan Yi et al: "Expression of an Anti–CD3 single–chain Immunotoxin With a Truncated Diphtheria Toxin in a Mutant CHO Cell Line." Protein Expression and Purification, vol. 19, No. 2, Jul. 2000, pp. 304–311.

DATABASE EMBL Online EBI; Feb. 9, 2000; "Mycoplasma Gallisepticum Gene for 120 kDa Membrane Protein", database accession No. AB023292 XP002226200.

DATABASE EMBL Online EBI; Apr. 9, 2000, "Mycoplasma Gallisepticum Gene for 120 kDa Membrane Protein Mgc3"; database accession No. AB033211 XP002226201.

* cited by examiner

*Primary Examiner*—James C. Housel
*Assistant Examiner*—Zachariah Lucas
(74) *Attorney, Agent, or Firm*—Armstrong, Kratz, Quintos, Hanson, & Brooks, LLP

(57) ABSTRACT

There is provided a DNA molecule derived from a prokaryotic cell in which at least one of the DNA regions encoding NXB (N is asparagine, X is any amino acid other than proline, and B is serine or threonine) has been modified so that no N-glycosylation occurs during the expression in a eukaryotic cell, and since the DNA molecule has been modified at the N-glycosylation site, it produces a non-N-glycosylated protein, which thereby exhibits a high immunogenicity when, for example, it is allowed to produce, in a eukaryotic cell, an antigen protein derived from a prokaryotic cell.

13 Claims, 5 Drawing Sheets

SEQUENCE LISTING

```
<160> NUMBER OF SEQ ID NOS: 4

<210> SEQ ID NO 1
<211> LENGTH: 1306
<212> TYPE: DNA
<213> ORGANISM: Mycoplasma gallisepticum
<220> FEATURE:
<223> OTHER INFORMATION: TTM-1 gene

<400> SEQUENCE: 1

aaaaacatca gattgttaat ctgatatctt tgcttaaaaa aacacaaaat cttctaacaa     60

aatcctaaat aaataagccg ttaaattaac taaaaaatta aaaaaatggt ttttcttatc    120

aaccaaaatt ctctagtaat aaacgcttat ttatttttat ttttagtcat cttttaagat    180

ataaatatat cttaatattc tatgaataag aaaagaatca tcttaaagac tattagtttg    240

ttaggtacaa catcctttct tagcattggg atttctagct gtatgtctat tactaaaaaa    300

gatgcaaacc caaataatgg ccaaacccaa ttagaagcag cgcgaatgga gttaacagat    360

ctaatcaatg ctaaagcgat gacattagct tcactacaag actatgccaa gattgaagct    420

agtttatcat ctgcttatag tgaagctgaa acagttaaca ataaccttaa tgcaacatta    480

gaacaactaa aaatggctaa aactaattta gaatcagcca tcaaccaagc taatacggat    540

aaaacgactt ttgataatga acacccaaat ttagttgaag catacaaagc actaaaaacc    600

actttagaac aacgtgctac taaccttgaa ggtttgtcat caactgctta taatcaaatt    660

cgcaataatt tagtggatct atacaataaa gctagtagtt taataactaa aacactagat    720

ccactaaatg gggggaacgct tttagattct aatgagatta ctacagttaa tcggaatatt    780

aataatacgt tatcaactat taatgaacaa aagactaatg ctgatgcatt atctaatagt    840

tttattaaaa aagtgattca aaataatgaa caaagttttg tagggacttt tacaaacgct    900

aatgttcaac cttcaaacta cagttttgtt gcttttagtg ctgatgtaac acccgtcaat    960

tataaatatg caagaaggac cgtttggaat ggtgatgaac cttcaagtag aattcttgca   1020

aacacgaata gtatcacaga tgtttcttgg atttatagtt tagctggaac aaacacgaag   1080

taccaattta gttttagcaa ctatggtcca tcaactggtt atttatattt cccttataag   1140

ttggttaaag cagctgatgc taataacgtt ggattacaat acaaattaaa taatggaaat   1200

gttcaacaag ttgagtttgc cacttcaact agtgcaaata atactacagc taatccaact   1260

ccagcagttg atgagattaa agttgctaaa atcgttttat caggtt                   1306
```

-continued

<210> SEQ ID NO 2
<211> LENGTH: 3189
<212> TYPE: DNA
<213> ORGANISM: Mycoplasma gallisepticum
<220> FEATURE:
<223> OTHER INFORMATION: mgc3 gene

<400> SEQUENCE: 2
atgaatattt ctaaaaaact taaaagttat acattgatag gtggattagc tgtatttgga 60
gctcttggtt ctgcaagctt tggctttaag caatcagata agagtaacga taacacgcaa 120
ttagttaatc aagcaagaac gctagatgct aattctgtta gacttgcagg tcttggacaa 180
aatggttcgt tgttcaatac agttcttaga gatgttgatg ataactttat aacagcagct 240
aatggaacaa ttatcaaatt agatagtttt actaaaccat tatatggttt agatctaagt 300
gatgattgtg gtggatacaa agtaaaacaa atagtttcag attacacaac tagcagaaat 360
agatttgatc aaagacaaac aagagcatat tatgctctgt tggttaatga tgaagctaac 420
gttcatttaa aaagaattaa tactaactca aatagaattg gtaatagaaa caacaattct 480
aagtttgtaa ttggtggtgt tgataatcca gctcacgtaa ttagatttac tgatgatggg 540
actaaattta attttacaaa ccaaactcaa ggtgaaattg ttaatgactt cattttagat 600
gcgccaatct tacctaaaga tttacaccca gattggtata acttatacat tcaaagaaag 660
atcttaccaa atgacgtcaa cactgcagtt gttccttggc cagtaggtag agttagtgga 720
acaaatgctg atgatgggat gtttgattgt gggaatggtc aaataactaa tacagatcct 780
attgctcaaa ctaaaaccac tactgataat caaaatcctt caacttttaa ttcaggagca 840
atgcctggtg caaacaatag atacgattct caattgaatg tcaagcatag aattaaaaca 900
tctttccaat tagatgaaaa atttgtttat ccagaatgga ctggttctga agagaataaa 960
aatattacaa gattagctac tggaagtttg ccaagcaacg aaagatattg gattcttgac 1020
atacccggga ctccacaagt tactttaaaa gaagattcag ttaacgtatt ttcaagacta 1080
tacttaaact cagttaattc tttatcattc attggtgata gtatttatat ttttggtacc 1140
tctgaattac catcattatg gtactattca ttcccaacta gattatctga tctaaccgct 1200
ttgaatcaag ttaaaacaga tgatattgaa gcttcaagca ctgataacgg tacaacaaca 1260
aacggaacaa cgacaacagc tgatacatct agtggttcaa caggtgctgg aacaggaaat 1320
actactaaca cttctcaaac agtttctaat cctactttaa atacttatcg tagttttgga 1380
attgatagta aaccaacttc tgcaaacaaa atagatgaaa ctaattgggc agatcctaac 1440
gttattgaag caagaatata tgctgaatac agattaggta ttcaaaatga aattccaata 1500
actaatgcag gaaactttat ccgaaacaca attggtggtg ttggttttac ttcaacaggt 1560
tcaagagtag ttttaagagc ttcttataac ggtgatcaac gtccaactgg aaacttccaa 1620
cctttcttat acgtatttgg ttatttagga taccaacaaa ctagaacagg aactttctgg 1680
tacggaacat ataagctttt aaacaacagc ccttacgacg tattagattc tccaagagta 1740
ggtactgaaa ccaatcaatt tagaagaact tcattaacat accctgttat gggtggatat 1800
ctaactgaag aaggtgctag aagtttctct aatactccat atataagagc acaaggtgac 1860
acaccagaaa gccgaagcat cttccaatct ggctattctg ataatactta tgagtacatt 1920
caatcagttt taggatttga tggaattaga aataacttaa atgttggggt taaagcatca 1980
agcttcttaa actcaaatag accaaatcca aacggtctag aaatgattgc tgcaacaaca 2040
tacttaagat cacaaattgg attagctaga acatctggat taccaaacca acaaccattc 2100

-continued

```
ggaacaactc accaagttat ttcagtatca cctggtgatc agttctcatc aattaagaat   2160

attagaacaa tcttccctgg taaccagtta tggtacttct tattcacaaa tgaaaataat   2220

aaatctagtg tttatacatt aagattagct gactcaagta accctgatgc gtcaagctca   2280

ttcagtccaa caagtttaat tgacgttaat gaaattggtg taatcttacc tttattagac   2340

aattcattct atacagtaaa tgctgctggt aatgttgcat tgttctcatc aaaccctggt   2400

tctcctggat catatactgc tgtaaataca tttaatcaga acttatctga tattgctttt   2460

gaaggttctg gtgctaagta tacatctgat ttctggggaa caatccaatt caaacccgat   2520

gagtacttaa ttcaaaatgg gttcactagt caagtggcta gaaacttcgt tacaaaccaa   2580

agcttcttaa acagtttagt tgacttcact cctgctaatg ctggtactaa ctaccgtgta   2640

gtggttgatc ctgatggtaa tttaacaaac caaaacctac ctctaaaagt tcagatccaa   2700

tacttagatg gtaagtatta tgatgctaaa ttaaagaaca ataatttagt aacattctct   2760

tataacaact ttggcgcctt accttcatgg gtagtgccta cagcaattgg tagtacatta   2820

ggtattcttg caattatgat catcttagga ttagctatcg gtattccttt aagagctcaa   2880

agaaaattac aagacaaagg gttcaaaaca acattcaaaa aagttgatac cttgactgct   2940

gctgttggtt cagtttacaa gaagattatt acccaaactg ctaacgttaa gaaaaaacct   3000

gctgctttag gtgctggtaa atctggtgat aagaaacctg ctgctgctgc taaacctgct   3060

gctccagcta aaccatctgc accaaaagct agctcaccag ctaaaccaac tgggcctaaa   3120

tctggtgcgc ctacaaaacc aactgctcct aagccagctg ctccaaaacc aaccgctccc   3180

aaagaataa                                                           3189
```

<210> SEQ ID NO 3
<211> LENGTH: 456
<212> TYPE: PRT
<213> ORGANISM: Mycoplasma gallisepticum
<220> FEATURE:
<223> OTHER INFORMATION: TTM-1 portion of pNZ40K-S

<400> SEQUENCE: 3

```
Met His Tyr Phe Arg Arg Asn Cys Ile Phe Phe Leu Ile Val Ile Leu
  1               5                  10                  15

Tyr Gly Thr Asn Ser Ser Pro Ser Thr Gln Asn Val Thr Ser Arg Glu
             20                  25                  30

Val Val Ser Ser Val Gln Leu Ser Glu Glu Glu Ser Thr Phe Tyr Leu
         35                  40                  45

Cys Pro Pro Pro Val Gly Ser Thr Val Ile Arg Leu Glu Phe Gly Cys
     50                  55                  60

Met Ser Ile Thr Lys Lys Asp Ala Asn Pro Asn Asn Gly Gln Thr Gln
 65                  70                  75                  80

Leu Glu Ala Ala Arg Met Glu Leu Thr Asp Leu Ile Asn Ala Lys Ala
                 85                  90                  95

Met Thr Leu Ala Ser Leu Gln Asp Tyr Ala Lys Ile Glu Ala Ser Leu
            100                 105                 110

Ser Ser Ala Tyr Ser Glu Ala Glu Thr Val Asn Asn Asn Leu Asn Ala
        115                 120                 125

Thr Leu Glu Gln Leu Lys Met Ala Lys Thr Asn Leu Glu Ser Ala Ile
    130                 135                 140

Asn Gln Ala Asn Thr Asp Lys Thr Thr Phe Asp Asn Glu His Pro Asn
145                 150                 155                 160

Leu Val Glu Ala Tyr Lys Ala Leu Lys Thr Thr Leu Glu Gln Arg Ala
```

-continued

```
                165                 170                 175

Thr Asn Leu Glu Gly Leu Ser Ser Thr Ala Tyr Asn Gln Ile Arg Asn
            180                 185                 190

Asn Leu Val Asp Leu Tyr Asn Lys Ala Ser Ser Leu Ile Thr Lys Thr
        195                 200                 205

Leu Asp Pro Leu Asn Gly Gly Thr Leu Leu Asp Ser Asn Glu Ile Thr
    210                 215                 220

Thr Val Asn Arg Asn Ile Asn Asn Thr Leu Ser Thr Ile Asn Glu Gln
225                 230                 235                 240

Lys Thr Asn Ala Asp Ala Leu Ser Asn Ser Phe Ile Lys Lys Val Ile
                245                 250                 255

Gln Asn Asn Glu Gln Ser Phe Val Gly Thr Phe Thr Asn Ala Asn Val
            260                 265                 270

Gln Pro Ser Asn Tyr Ser Phe Val Ala Phe Ser Ala Asp Val Thr Pro
        275                 280                 285

Val Asn Tyr Lys Tyr Ala Arg Arg Thr Val Trp Asn Gly Asp Glu Pro
    290                 295                 300

Ser Ser Arg Ile Leu Ala Asn Thr Asn Ser Ile Thr Asp Val Ser Trp
305                 310                 315                 320

Ile Tyr Ser Leu Ala Gly Thr Asn Thr Lys Tyr Gln Phe Ser Phe Ser
                325                 330                 335

Asn Tyr Gly Pro Ser Thr Gly Tyr Leu Tyr Phe Pro Tyr Lys Leu Val
            340                 345                 350

Lys Ala Ala Asp Ala Asn Asn Val Gly Leu Gln Tyr Lys Leu Asn Asn
        355                 360                 365

Gly Asn Val Gln Gln Val Glu Phe Ala Thr Ser Thr Ser Ala Asn Asn
    370                 375                 380

Thr Thr Ala Asn Pro Thr Pro Ala Val Asp Glu Ile Lys Val Ala Lys
385                 390                 395                 400

Ile Val Leu Ser Gly Leu Arg Phe Gly Gln Asn Thr Ile Glu Leu Ser
                405                 410                 415

Val Pro Thr Gly Glu Gly Asn Met Asn Lys Val Ala Pro Met Ile Gly
            420                 425                 430

Asn Ile Tyr Leu Ser Ser Asn Glu Asn Asn Ala Asp Lys Ile Pro Gly
        435                 440                 445

Tyr Arg Arg Pro Gly Thr Phe Leu
    450                 455


<210> SEQ ID NO 4
<211> LENGTH: 1224
<212> TYPE: PRT
<213> ORGANISM: Mycoplasma gallisepticum
<220> FEATURE:
<223> OTHER INFORMATION: MGC3 encoded by mgc3 gene

<400> SEQUENCE: 4

Met Asn Ile Ser Lys Lys Leu Lys Ser Tyr Thr Leu Ile Gly Gly Leu
  1               5                  10                  15

Ala Val Phe Gly Ala Leu Gly Ser Ala Ser Phe Gly Phe Lys Gln Ser
            20                  25                  30

Asp Lys Ser Asn Asp Asn Thr Gln Leu Val Asn Gln Ala Arg Thr Leu
        35                  40                  45

Asp Ala Asn Ser Val Arg Leu Ala Gly Leu Gly Gln Asn Gly Ser Leu
    50                  55                  60

Phe Asn Thr Val Leu Arg Asp Val Asp Asp Asn Phe Ile Thr Ala Ala
```

-continued

```
65                  70                  75                  80

Asn Gly Thr Ile Ile Lys Leu Asp Ser Phe Thr Lys Pro Leu Tyr Gly
                85                  90                  95

Leu Asp Leu Ser Asp Asp Cys Gly Gly Tyr Lys Val Lys Gln Ile Val
            100                 105                 110

Ser Asp Tyr Thr Thr Ser Arg Asn Arg Phe Asp Gln Arg Gln Thr Arg
        115                 120                 125

Ala Tyr Tyr Ala Leu Leu Val Asn Asp Glu Ala Asn Val His Leu Lys
    130                 135                 140

Arg Ile Asn Thr Asn Ser Asn Arg Ile Gly Asn Arg Asn Asn Asn Ser
145                 150                 155                 160

Lys Phe Val Ile Gly Gly Val Asp Asn Pro Ala His Val Ile Arg Phe
                165                 170                 175

Thr Asp Asp Gly Thr Lys Phe Asn Phe Thr Asn Gln Thr Gln Gly Glu
            180                 185                 190

Ile Val Asn Asp Phe Ile Leu Asp Ala Pro Ile Leu Pro Lys Asp Leu
        195                 200                 205

His Pro Asp Trp Tyr Asn Leu Tyr Ile Gln Arg Lys Ile Leu Pro Asn
    210                 215                 220

Asp Val Asn Thr Ala Val Val Pro Trp Pro Val Gly Arg Val Ser Gly
225                 230                 235                 240

Thr Asn Ala Asp Asp Gly Met Phe Asp Cys Gly Asn Gly Gln Ile Thr
                245                 250                 255

Asn Thr Asp Pro Ile Ala Gln Thr Lys Thr Thr Thr Asp Asn Gln Asn
            260                 265                 270

Pro Ser Thr Phe Asn Ser Gly Ala Met Pro Gly Ala Asn Asn Arg Tyr
        275                 280                 285

Asp Ser Gln Leu Asn Val Lys His Arg Ile Lys Thr Ser Phe Gln Leu
    290                 295                 300

Asp Glu Arg Ile Asn Thr Asn Ser Asn Arg Ile Gly Asn Arg Asn Asn
305                 310                 315                 320

Asn Ser Lys Phe Val Ile Gly Gly Val Asp Asn Pro Ala His Val Ile
                325                 330                 335

Arg Phe Thr Asp Asp Gly Thr Lys Phe Asn Phe Thr Asn Gln Thr Gln
            340                 345                 350

Gly Glu Ile Val Asn Asp Phe Ile Leu Asp Ala Pro Ile Leu Pro Lys
        355                 360                 365

Asp Leu His Pro Asp Trp Tyr Asn Leu Tyr Ile Gln Arg Lys Ile Leu
    370                 375                 380

Pro Asn Asp Val Asn Thr Ala Val Val Pro Trp Pro Val Gly Arg Val
385                 390                 395                 400

Ser Gly Thr Asn Ala Asp Asp Gly Met Phe Asp Cys Gly Asn Gly Gln
                405                 410                 415

Ile Thr Asn Thr Asp Pro Ile Ala Gln Thr Lys Thr Thr Thr Asp Asn
            420                 425                 430

Gln Asn Pro Ser Thr Phe Asn Ser Gly Ala Met Pro Gly Ala Asn Asn
        435                 440                 445

Arg Tyr Asp Ser Gln Leu Asn Val Lys His Arg Ile Lys Thr Ser Phe
    450                 455                 460

Gln Leu Asp Glu Lys Phe Val Tyr Pro Glu Trp Thr Gly Ser Glu Glu
465                 470                 475                 480

Asn Lys Asn Ile Thr Arg Leu Ala Thr Gly Ser Leu Pro Ser Asn Glu
                485                 490                 495
```

-continued

```
Arg Tyr Trp Ile Leu Asp Ile Pro Gly Thr Pro Gln Val Thr Leu Lys
            500                 505                 510

Glu Asp Ser Val Asn Val Phe Ser Arg Leu Tyr Leu Asn Ser Val Asn
        515                 520                 525

Ser Leu Ser Phe Ile Gly Asp Ser Ile Tyr Ile Phe Gly Thr Ser Glu
    530                 535                 540

Leu Pro Ser Leu Trp Tyr Tyr Ser Phe Pro Thr Arg Leu Ser Asp Leu
545                 550                 555                 560

Thr Ala Leu Asn Gln Val Lys Thr Asp Asp Ile Glu Ala Ser Ser Thr
                565                 570                 575

Asp Asn Gly Thr Thr Thr Asn Gly Thr Thr Thr Thr Ala Asp Thr Ser
            580                 585                 590

Ser Gly Ser Thr Gly Ala Gly Thr Gly Asn Thr Thr Asn Thr Ser Gln
        595                 600                 605

Thr Val Ser Asn Pro Thr Leu Asn Thr Tyr Arg Ser Phe Gly Ile Asp
    610                 615                 620

Ser Lys Pro Thr Ser Ala Asn Lys Ile Asp Glu Thr Asn Trp Ala Asp
625                 630                 635                 640

Pro Asn Val Ile Glu Ala Arg Ile Tyr Ala Glu Tyr Arg Leu Gly Ile
                645                 650                 655

Gln Asn Glu Ile Pro Ile Thr Asn Ala Gly Asn Phe Ile Arg Asn Thr
            660                 665                 670

Ile Gly Gly Val Gly Phe Thr Ser Thr Gly Ser Arg Val Val Leu Arg
        675                 680                 685

Ala Ser Tyr Asn Gly Asp Gln Arg Pro Thr Gly Asn Phe Gln Pro Phe
    690                 695                 700

Leu Tyr Val Phe Gly Tyr Leu Gly Tyr Gln Gln Thr Arg Thr Gly Thr
705                 710                 715                 720

Phe Trp Tyr Gly Thr Tyr Lys Leu Leu Asn Asn Ser Pro Tyr Asp Val
                725                 730                 735

Leu Asp Ser Pro Arg Val Gly Thr Glu Thr Asn Gln Phe Arg Arg Thr
            740                 745                 750

Ser Leu Thr Tyr Pro Val Met Gly Gly Tyr Leu Thr Glu Glu Gly Ala
        755                 760                 765

Arg Ser Phe Ser Asn Thr Pro Tyr Ile Arg Ala Gln Gly Asp Thr Pro
    770                 775                 780

Glu Ser Arg Ser Ile Phe Gln Ser Gly Tyr Ser Asp Asn Thr Tyr Glu
785                 790                 795                 800

Tyr Ile Gln Ser Val Leu Gly Phe Asp Gly Ile Arg Asn Asn Leu Asn
                805                 810                 815

Val Gly Val Lys Ala Ser Ser Phe Leu Asn Ser Asn Arg Pro Asn Pro
            820                 825                 830

Asn Gly Leu Glu Met Ile Ala Ala Thr Thr Tyr Leu Arg Ser Gln Ile
        835                 840                 845

Gly Leu Ala Arg Thr Ser Gly Leu Pro Asn Gln Gln Pro Phe Gly Thr
    850                 855                 860

Thr His Gln Val Ile Ser Val Ser Pro Gly Asp Gln Phe Ser Ser Ile
865                 870                 875                 880

Lys Asn Ile Arg Thr Ile Phe Pro Gly Asn Gln Leu Trp Tyr Phe Leu
                885                 890                 895

Phe Thr Asn Glu Asn Asn Lys Ser Ser Val Tyr Thr Leu Arg Leu Ala
            900                 905                 910
```

-continued

```
Asp Ser Ser Asn Pro Asp Ala Ser Ser Ser Phe Ser Pro Thr Ser Leu
        915                 920                 925

Ile Asp Val Asn Glu Ile Gly Val Ile Leu Pro Leu Leu Asp Asn Ser
    930                 935                 940

Phe Tyr Thr Val Asn Ala Ala Gly Asn Val Ala Leu Phe Ser Ser Asn
945                 950                 955                 960

Pro Gly Ser Pro Gly Ser Tyr Thr Ala Val Asn Thr Phe Asn Gln Asn
                965                 970                 975

Leu Ser Asp Ile Ala Phe Glu Gly Ser Gly Ala Lys Tyr Thr Ser Asp
            980                 985                 990

Phe Trp Gly Thr Ile Gln Phe Lys Pro Asp Glu Tyr Leu Ile Gln Asn
        995                 1000                1005

Gly Phe Thr Ser Gln Val Ala Arg Asn Phe Val Thr Asn Gln Ser Phe
   1010                1015                1020

Leu Asn Ser Leu Val Asp Phe Thr Pro Ala Asn Ala Gly Thr Asn Tyr
1025                1030                1035                1040

Arg Val Val Val Asp Pro Asp Gly Asn Leu Thr Asn Gln Asn Leu Pro
               1045                1050                1055

Leu Lys Val Gln Ile Gln Tyr Leu Asp Gly Lys Tyr Tyr Asp Ala Lys
           1060                1065                1070

Leu Lys Asn Asn Asn Leu Val Thr Phe Ser Tyr Asn Asn Phe Gly Ala
       1075                1080                1085

Leu Pro Ser Trp Val Val Pro Thr Ala Ile Gly Ser Thr Leu Gly Ile
   1090                1095                1100

Leu Ala Ile Met Ile Ile Leu Gly Leu Ala Ile Gly Ile Pro Leu Arg
1105                1110                1115                1120

Ala Gln Arg Lys Leu Gln Asp Lys Gly Phe Lys Thr Thr Phe Lys Lys
               1125                1130                1135

Val Asp Thr Leu Thr Ala Ala Val Gly Ser Val Tyr Lys Lys Ile Ile
           1140                1145                1150

Thr Gln Thr Ala Asn Val Lys Lys Lys Pro Ala Ala Leu Gly Ala Gly
       1155                1160                1165

Lys Ser Gly Asp Lys Lys Pro Ala Ala Ala Ala Lys Pro Ala Ala Pro
   1170                1175                1180

Ala Lys Pro Ser Ala Pro Lys Ala Ser Ser Pro Ala Lys Pro Thr Gly
1185                1190                1195                1200

Pro Lys Ser Gly Ala Pro Thr Lys Pro Thr Ala Pro Lys Pro Ala Ala
               1205                1210                1215

Pro Lys Pro Thr Ala Pro Lys Glu
           1220
```

MODIFIED DNA MOLECULE, RECOMBINANT CONTAINING THE SAME, AND USES THEREOF

TECHNICAL FIELD

The present invention relates to an modified gene derived from a prokaryotic cell (including an organism comprising prokaryotic cells) said gene capable of producing a protein that has no sugar chain additions when expressed in a eukaryotic cell (including an organism comprising eukaryotic cells), and uses thereof.

BACKGROUND

As methods of obtaining gene products of prokaryotic cells such as bacteria and blue-green algae, there have conventionally been used methods of culturing prokaryotic cells having said gene and then isolating and purifying the gene products of interest. However, when the gene product thus obtained is used as a vaccine, such methods had a problem of production efficiency in which an adequate amount of expression cannot be secured, and a safety problem due to difficulty in removing impurities such as pyrogens in the purification process.

Thus, focusing on the advantage of obviating the need of removing pyrogens, attempts have been made to introduce into a eukaryotic cell a recombinant vector in which the gene of interest derived from a prokaryotic cell has been integrated into a vector such as a virus, and then allowing the gene to be directly expressed in the eukaryotic cell. However, since prokaryotic cells and eukaryotic cells are essentially different in their mode of gene expression, gene products of a prokaryotic cell expressed in a eukaryotic cell could not exhibit the activity at a level equivalent to those produced in the prokaryotic cell, which sometimes resulted in an inadequate immunogenicity.

For example, U.S. Pat. No. 5,871,742 describes that an avipoxvirus vector which has integrated an antigen gene TTM-1 (TTM-1 gene) derived from *Mycoplasma gallisepticum* is effective as a vaccine to protect against *Mycoplasma gallisepticum* infection. Subsequently, it was found that the product (TTMG-1 antigen) of the TTM-1 gene is displayed on the cell membrane when the TTM-1 gene is expressed in the prokaryotic cell, whereas the TTM-1 product expressed in a eukaryotic cell is not displayed on the cell membrane of the eukaryotic cell and thereby is unlikely to exhibit the inherent immunogenicity. As a result of further study, in order to display the TTM-1 product on the surface of eukaryotic cells, a fusion gene was constructed in which a DNA encoding a virus-derived type II signal sequence such as signal sequence (hereinafter referred to as MDV gB signal) of gB of Marek's disease virus (MDV) has been ligated to said gene. By integrating this fusion gene into avipoxvirus and allowing it to be expressed, the TTMG-1 antigen was successfully displayed on the surface of the cell membrane, and thereby a vaccine that exhibits a higher activity of protecting against infection was obtained (International Patent Publication WO97/36924).

In most cases, proteins synthesized in the eukaryotic cell are different from those synthesized in the prokaryotic cell in that the former has sugar chains attached thereto.

Yoshida et al. (2000) constructed a recombinant avipoxvirus in which mgc3 (the mgc3 gene), a gene derived from *Mycoplasma gallisepticum*, other than the TTM-1 gene was integrated, and investigated the expression of the product (the MGC3 antigen) of the mgc 3 gene by immunoprecipitation. As a result, it was confirmed that N-linked sugar chains are not attached (N-glycosylated) to the MGC3 antigen having no MDVgB signal added thereto whereas the MDVgB signal-added MGC3 antigen undergoes N-glycosylation. Yoshida et al. (2000) also confirmed that the MGC3 fusion protein produced by a recombinant avipoxvirus that has integrated therein a fusion gene of the mgc3 gene and DNA encoding the MDVgB signal is 50-fold more reactive to a monoclonal antibody 35A6 that recognizes the MGC3 protein than the MGC3 antigen produced by a recombinant avipoxvirus that has integrated therein only the antigen gene mgc3. Based on this, it had been thought that though the fusion of a DNA encoding the MDVgB signal with the antigen gene may result in the addition of sugars to the protein obtained, a highly immunogenic protein could be obtained without N-glycosylation affecting immunogenicity.

DISCLOSURE OF INVENTION

However, the inventors of the present invention have performed an animal experiment in which chickens were inoculated with a recombinant virus prepared according to Yoshida et al. (2000) by integrating the antigen gene of *Mycoplasma gallisepticum* to which a DNA encoding the MDVgB signal had been added, and thereby confirmed that no significant enhancement in the effect of protecting against infection was observed compared to when the DNA encoding the MDVgB signal was not added.

This result demonstrated that the use of a fusion gene to which a signal-encoding DNA is added does not always produce enhanced immunogenicity.

Accordingly, after intensive study in order to obtain a novel vaccine having an enhanced immunogenicity, the inventors of the present invention have found that the antigen protein that should inherently be produced by the prokaryote, i.e. an antigen protein that is not N-glycosylated, provides a high immunogenicity, and thereby have completed the present invention.

Thus, according to the present invention:

Firstly, there is provided a DNA molecule derived from a prokaryotic cell in which at least one of the DNA regions encoding NXB (N is asparagine, X is any amino acid other than proline, and B is serine or threonine) has been modified so that no N-glycosylation occurs during the expression in the eukaryotic cell;

secondly, there is provided a fused DNA molecule in which a DNA encoding a signal sequence is ligated to the N-terminal end of said modified DNA molecule so that it may be expressed as a fusion protein;

thirdly, there is provided a recombinant virus that has integrated therein (1) a DNA molecule in which at least one of the DNA regions encoding NXB (N is asparagine, X is any amino acid other than proline, and B is serine or threonine) has been modified so that no N-glycosylation occurs during the expression in the eukaryotic cell, or (2) a fused DNA molecule in which a DNA encoding a signal sequence is ligated to the N-terminal end of said modified DNA molecule so that it may be expressed as a fusion protein;

fourthly, there is provided a method of producing a protein encoded by said modified DNA molecule or said fused DNA molecule using said recombinant virus in a eukaryotic cell; and fifthly, there is provided a vaccine that uses said recombinant virus.

BEST MODE FOR CARRYING OUT THE INVENTION

Figure 1:
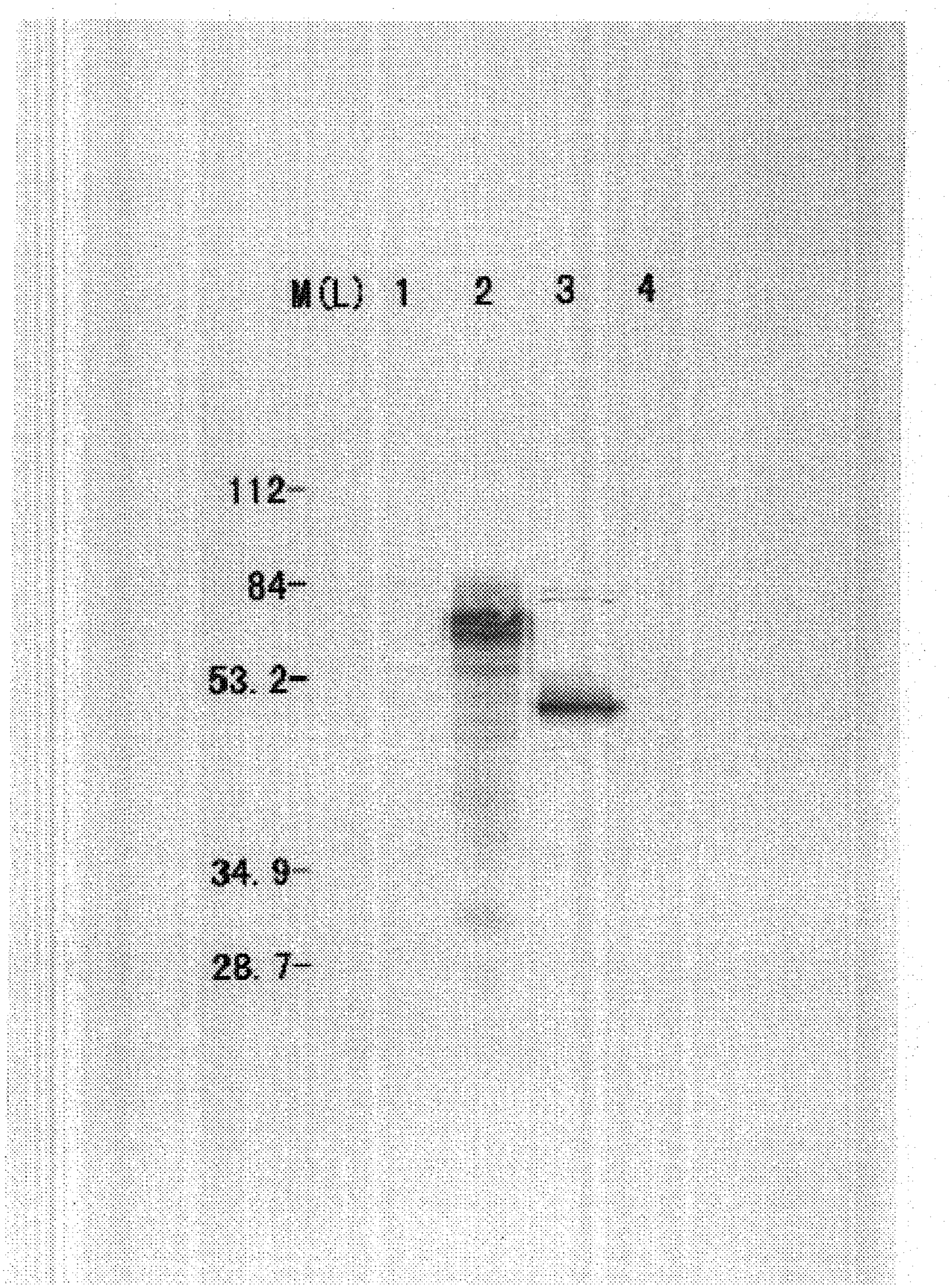
FIG. 1 is a Western blot that compares the molecular weight detected using anti-TTMG-1 antiserum of the non-N-glycosylated TTMG-1 antigen (lane 3) expressed from a recombinant virus containing the modified DNA and the N-glycosylated TTMG-1 antigen (lane 2) expressed from a recombinant virus containing the unmodified DNA. In this figure, lane 1 indicates the result from the virus (negative control) containing no antigen gene and lane 4 indicates the result of the MGC3 antigen that cannot be detected with the anti-TTMG-1 antiserum.

In accordance with the present invention, the amino acid sequence represented by NXB (N is asparagine, X is any amino acid other than proline, and B is serine or threonine) is an amino acid that is present in a peptide encoded by a DNA molecule derived from a prokaryotic cell and that is recognized as a N-glycosylation site in a eukaryotic cell. According to the present invention, this amino acid sequence is sometimes referred to as "a potential N-glycosylation site".

Known as such are an amino acid sequence represented by N (asparagine)-X (X is any amino acid other than proline)-S (serine), or an amino acid sequence represented by N (asparagine)-X (X is any amino acid other than proline)-T (threonine).

In accordance with the present invention, the DNA region that is modified so as not to be N-glycosylated (the addition of a N-linked sugar chain) is a DNA region that encodes one or more N-glycosylation sites present in the gene derived from a prokaryotic cell. When a DNA region encoding a plurality of N-glycosylation sites is present in the gene of a prokaryotic cell, the DNA region encoding the N-glycosylation site that is displayed on the surface may be only modified considering the conformation of the protein finally obtained, or all such regions present in said gene may be modified.

Modified DNA Molecule

The modified DNA molecule of the present invention is a DNA molecule in which at least one region among the DNA regions encoding potential N-glycosylation sites present in the gene derived from a prokaryotic cell has been modified so that N-glycosylation does not occur during the expression in a eukaryotic cell for.

(Prokaryotic Cell)

According to the present invention, prokaryotic cells may be bacteria or blue green algae, and pathogenic bacteria are suitable for the purpose of the present invention. For example, there can be mentioned gram-positive bacteria such as *Staphylococcus aureus, Clostridium tetani*, and *Clostridium botulinum*; gram-negative bacteria such as *Escherichia coli*, Salmonella, Haemophilus, and Bordetella; acid-fast bacteria such as *Mycobacterium tuberculosis*; and Mycoplasma, and preferably there can be mentioned Mycoplasma having pathogenically against avians.

(The Prokaryotic Cell-derived Gene to be the Target of Alteration)

According to the present invention, the prokaryotic cell-derived gene to be the target of alteration is a portion of the gene that is owned by the above prokaryotic cell and that contains the gene region encoding gene products such as protein. When it is used as vaccine specifically, the gene preferably contains a portion having all or one or more epitopes of the antigen gene that encodes the antigen protein.

As the antigen gene, there can be mentioned adhesin present in various bacteria, and more preferably genes encoding Pertactin, Fimbriae, Filamentous hemagglutinin (FHA) from Bordetella, the TTM-1 gene as set forth in SEQ ID NO: 1 that encodes the TMG-1 antigen (29 kd) described in U.S. Pat. No. 5,766,594, the TTMG-1 antigen (40 kd) described in U.S. Pat. No. 5,489,430, and the TM-66 antigen (66 kd) or TM-67 antigen (67 kd) described in U.S. Pat. No. 5,871,742, and the mgc3 gene as set forth in SEQ ID NO: 2 (GeneBank accession No. AB023292) encoding the M11 antigen (this is identical with the MGC3 antigen used by Yoshida et al.) described in International Patent Publication WO97/24370.

By analyzing the base sequence of the prokaryotic cell-derived gene to be the target of alteration and estimating the amino acid sequence from the sequence, it is possible to specify the DNA region that encodes the potential N-glycosylation site in said gene.

When a translation codon inherent to the prokaryotic cell is present in said gene used, this portion can be modified as needed. In the case of genes derived from Mycoplasma, for example, the base sequence "TGA" that should be read as the terminal codon in the usual prokaryotic cell is translated as tryptophan, and thus this "TGA" can be modified so that it may be translated as an amino acid (when TGA is to be translated as tryptophan, it is changed to TGG) in the eukaryotic cell.

Furthermore, when poxvirus is used to express protein, the base sequence "T5NT" is likely to become a translational termination signal (Yanagida et al., 1992), it is preferred to alter so that it is not accompanied by amino acid substitution in order to prevent the termination of translation.

In addition, as reported that after the Gp120 gene of HIV was converted to a human optimized codon, its effect as a DNA vaccine increased (Andre et al., 1998), the amount expressed of a gene can be enhanced by replacing with a translation codon (optimization of codon) of an amino acid that is highly frequently used in the living body in which the DNA molecule is to be expressed. Accordingly, when the DNA molecule of the present invention is to be expressed in chickens, it is likely that optimization to a chicken codon can enhance the gene expression, and the alteration to a chicken codon can be performed as needed.

(Method of Altering the N-glycosylation Site)

As the method of altering the N-glycosylation site in the prokaryotic cell-derived gene, there can be mentioned the following three alteration methods:

(1) the alteration of the DNA sequence encoding asparagine (N) to a DNA sequence encoding an amino acid other than asparagine;

(2) the alteration of the DNA sequence encoding any amino acid (X) other than proline to a DNA sequence encoding proline; and (3) the alteration of the DNA sequence encoding serine or threonine (B) to a DNA sequence encoding an amino acid other than serine or threonine.

Among these three methods, the method of (1) in which the DNA sequence encoding asparagine (N) is changed to a DNA sequence encoding glutamine (Q) is preferred in that it does not affect protein conformation.

These methods of altering genes are not specifically limited. For example, methods using synthetic DNA such as in vitro mutagenesis and polymerase chain reaction (PCR) are commonly used. From the viewpoint that a plurality of mutations can introduced and in a shorter time as well, the method of using PCR is preferred.

Fused DNA Molecule

In the fused DNA molecule of the present invention, a DNA encoding a signal sequence has been ligated to the N-terminal end of the above DNA molecule of the present invention so that it may be expressed as a fusion protein.

The ligation of a DNA encoding a signal sequence to the N-terminal end of the DNA molecule of the present invention followed by the expression of the fusion protein makes it possible to obtain a vaccine having a higher immunogenicity.

(Signal Sequence and DNA Encoding the Same)

Signal sequences and methods of ligating the DNA encoding the same to another DNA molecule have been described in detail in U.S. Pat. No. 5,871,742, International Patent Publication WO97/36924, and Yoshida et al. (2000), and are briefly explained hereinbelow.

Signal sequences are sequences that function when membrane proteins of viruses etc. are extracellularly secreted or displayed. The membrane protein from which signal sequences are derived may be either type I or type II. Examples of membrane proteins include the hemagglutinin neuraminidase (HN) protein of Newcastle disease virus NDV), the gB protein of herpes simplex virus (HSV) type 1 and Marek's disease virus (MDV) type I, the *G glycoprotein* of Rabies virus, and the like. Signal sequences can be readily found by analyzing the amino acid sequence of the hydrophobic peptide region in the amino terminal or the carboxy terminal of the membrane protein.

DNA encoding the signal sequence thus specified may be obtained by a conventional method, and ligated to the DNA molecule of the present invention to obtain the fused DNA molecule of the present invention. At this time, in order to allow the expression as a fusion protein, the signal sequence is ligated to the N-terminal end of the DNA molecule using a conventional method in such a manner that the open reading frame (ORF) estimated by analyzing the base sequence of the DNA molecule becomes aligned in frame.

When a potential N-glycosylation site is present in such a signal sequence, it is preferred to alter the DNA encoding the signal sequence as for the DNA molecule of the present invention in a similar manner as described above so that it may be not recognized as a N-glycosylation site when expressed in a eukaryotic cell.

Recombinant Virus

The recombinant virus of the present invention has integrated in the genome thereof the DNA molecule or the fused DNA molecule (hereinafter referred to collectively as the "DNA molecule" of the present invention).

When the DNA molecule of the present invention is to be integrated in the recombinant virus, it is usually integrated to be placed under the control of a regulatory gene (promoter) in order to obtain a high amount of expression. The promoter may be commonly used one that functions in the eukaryotic cell, and may be derived from a eukaryotic cell or virus. Specific examples of promoters include thymidine kinase promoter of herpesvirus (Ross et al., 1993), the gB protein promoter of the herpesvirus of turkey (HVT) and Marek's disease virus (MDV) serotype I (Ross et al., 1993), the IE promoter of human cytomegalovirus (HCMV) (Stinski et al., 1995), SV40 promoter (Gunning et al., 1987), human β actin promoter (Gunning et al., 1987), chicken β actin promoter (Kost et al.; 1983), the LTR promoter of Rous sarcoma virus (RSV) (Greuel et al., 1990), chimera promoter (Japanese Unexamined Patent Publication (Kokai) No. 2001-188), and the like.

By adding an enhancer, a factor that activates transcription, in addition to promoter, a more efficient expression may be predicted (Stinski et al., 1995). As the enhancer, there can be mentioned a portion of the cytomegalovirus-derived promoter, and generally the positional relationship to the inserted gene is not limited.

Furthermore, in the case of a recombinant herpesvirus, a higher amount of expression is obtained by adding DNA encoding a polyadenylation signal to the downstream of the DNA molecule of the present invention. As the polyadenylation signal, there can be illustrated the Poly A signal (Gunning et al., 1987) of SV40 etc. and the Poly A signal (Yanagida et al., 1993) of UL46h, UL47h and UL49h of Marek's disease virus (MDV) serotype I.

The method of obtaining the recombinant virus of the present invention is not specifically limited, and for example there is the method of homologous recombination between a vector in which any DNA (the DNA inserted into virus is hereinafter referred to collectively as foreign gene) such as the DNA molecule of the present invention and a promoter was sandwiched in between the fragments of the gene region that is not essential for the viral replication.

The recombinant virus of the present invention will now be explained in detail with reference to the example of a recombinant herpesvirus and a recombinant poxvirus.

(Recombinant Virus)

As the gene region nonessential for the growth of herpesvirus in the case of Marek's disease virus (MDV) serotype I, serotype II, serotype III (type III is turkey herpesvirus), there can be illustrated the TK region (Ross L. et al., 1991), US10 region (Sakaguchi M. et al., 1994), the US2 region (Sondermeijer, P. j. et al., 1993), the region in between UL44 and UL45 and the region in between UL45 and UL46 (a sequence from UL44 to UL46 (UVT-UL44–46insertion site) described in International Patent Publication WO99/18215.

A transfer vector for recombination is constructed that has a DNA region in which necessary foreign genes such as the DNA of the present invention and promoters are sandwiched by the nonessential region. The length of the region into which foreign genes such as the DNA of the present invention are inserted is, but not limited to, about 10 bp each in front of and behind the foreign gene insertion site, preferably 100 bp or longer, more preferably 500 bp or longer. The vector may be one that is generally used for the construction of recombinant virus, and include, for example, plasmid such as pBR322, pBR325, pBR327, pBR328, pUC8, pUC18, and pUC19, and phage such as λ phage and M13 phage, and cosmid such as pHC9.

Homologous recombination between this recombinant vector and the parent herpesvirus is allowed to take place to construct a recombinant herpesvirus.

The parent herpesvirus may be any herpesvirus that infects mammals or avians. In order to obtain avian vaccines, Marek's disease virus is preferably selected. There are three types of Marek's disease virus: serotype I, II, and III, any of which may be used to obtain the recombinant herpesvirus of the present invention. These Marek's disease viruses may be naturally occurring ones or may be those available from ATCC etc. with or without charge, and most preferably they are non-phathogenic. As such viruses, there can be illustrated the CVI988 (Rispens) strain for Marek's disease virus serotype I, the SB-1 strain for Marek's disease virus serotype II, and FC126 (ATCC VR-584B), PB-THV1, H-2, YT-7, and HPRS-26 for Marek's disease virus serotype III (HVT).

Specific examples for generating recombinant herpesvirus include those described below.

A recombinant vector in which the above-mentioned foreign gene has been sandwiched in a nonessential insertion site is introduced into a herpesvirus-infected cell by electroporation, the calcium phosphate method, a method that uses lipofectin, the gene gun method, and the like. In the case of avian herpesviruses, for example, cells to which herpesvirus is infected are preferably derived from avians, and include, for example, chick embryo fibroblasts (CEFs), developing chicken embryos, and chicken kidney cells. Culturing of infected cells may be performed by a commonly used method. As the method of introducing a recombinant vector into infected cells, electroporation and a method that employs lipofectin are preferably adopted because of their high efficiency of introduction. When the amount of plasmid introduced is in the range of 0.1 to 1000 μg, the incidence of recombinant virus between the genomic DNA of herpesvirus and the homologous region of the recombinant vector becomes higher. In order to select only recombinant viruses that have introduced such a plasmid, the Black Plaque Assay (BPA) can be used. The BPA method is one in which the foreign gene product and an antibody against this are reacted, to which an enzyme-labeled second antibody is reacted, and then the substrate for said enzyme is used to visualize plaques that expressed the products of the foreign gene. Using this method, a recombinant virus that expressed the foreign antigen gene may be selected. When these recombinant viruses are constructed, due to ease of detection, a marker gene such as β-galactosidase may be integrated as one of the foreign genes, in which expression is easily monitored using Bluo-Gal (manufactured by Gibco BRL) to isolate a recombinant. In addition, the method of plaque hybridization etc. may be used to isolate the recombinant herpesvirus of interest. By repeating these procedures, recombinant virus is purified.

(Recombinant Poxvirus)

Recombinant poxvirus can be constructed, in a similar manner to the construction of recombinant herpesvirus, using homologous recombination.

However, since poxvirus per se has a transcription factor etc. and thus transcription and translation are likely to occur by constituents of the virus per se. Therefore, the promoter used is not the one mentioned above as usable for the construction of the above recombinant herpesvirus but must be changed to a promoter for poxvirus. As the promoter for poxvirus, a synthetic promoter that functions as a promoter in the virus belonging to the poxvirus with reference to Davison et al. 1 and 2 (1989), or a natural promoter of poxvirus may be used. As the natural promoter of poxvirus, there can be mentioned the 7.5K promoter, 19K polypeptide promoter, 42K polypeptide promoter, 28K polypeptide promoter, and TK promoter (Weir et al., 1984) of vaccinia virus.

When a recombinant poxvirus is used for the expression of proteins, as described above, the foreign gene used is preferably modified at the T5NT region.

As the gene region nonessential for the growth of poxvirus, there can be used the TK gene region of fowlpox virus, pigeon poxvirus, quail pox (?), turkey poxvirus etc., the region in between the open reading frames (ORF) as described in U.S. Pat. No. 5,180,675 and Japanese Patent Publication No. 2766984, and the region described in U.S. Pat. No. 5,387,519. More specifically, an EcoRI fragment (7.3 kbp), an EcoRI-HindIII fragment (about 5.0 kbp), a BamHI fragment (about 4.0 kbp), and a HindIII fragment (about 5.2 kbp) derived from pigeon pox described in U.S. Pat. No. 5,387,519, and SpeI-HpaI (3026 bp) (FPV-29 insertion) in an EcoRI fragment (7.3 kbp).

Production of Proteins

By infecting the recombinant virus of the present invention to the cells in which said virus can infect and propagate, and culturing the cells, the DNA molecule derived from a prokaryotic cell integrated into the recombinant virus may be expressed and the protein encoded by said DNA molecule can be obtained.

The cells to which the virus is infected used may be the same cells as those used in the construction of the recombinant virus mentioned above. The culture conditions are the same as well.

The method of purifying the protein obtained is not specifically limited, and may be isolated and purified according to the description in, for example, Methods in Enzymology, Vol. 182 ("Guide to Protein Purification", Murry P. Desutscher ed., published by Academic Press).

The antigen peptide thus obtained may be diluted according to a conventional method, or mixed with a suitable adjuvant, and may be used as a component vaccine. As the adjuvant used, there can be illustrated Freund's complete adjuvant, Freund's incomplete adjuvant, alum, Arlacel, and the like. The mixed ratio with the adjuvant is, but not limited to, generally 1:1. When used as a component vaccine, 0.1 μg or more per individual, for chicken for example, may be administered, and there is no specific upper limit unless acute toxicity manifests. The method of administration may be subcutaneous, intravenous, intramuscular, or intraperitoneal injection, a method of immunizing by spraying into the airway, administration by drinking water and the like.

Vaccine (Recombinant Herpesvirus Vaccine)

The method of preparing live vaccine comprising a recombinant herpesvirus as a main ingredient is not specifically limited. For example, the following method may be used for preparation.

The recombinant herpesvirus of the present invention is infected to the cells (hereinafter referred to as host cells) in which said virus can grow, and after the cells have grown, they are scraped using a scraper or trypsin, and then centrifuged to separate the supernatant from the infected cells. In the case of avian herpesvirus, for example, the host cell used is preferably one derived from avians and CEF, chicken kidney cells etc. are preferably used. The infected cells thus obtained are suspended into a culture medium containing 10% dimethyl sulfoxide (DMSO), and stored in the presence of liquid nitrogen. When used as vaccine, the frozen product is thawed and dissolved in 100 volumes of phosphate buffer or physiological saline and used.

Stabilizers and other components for storing the above infected cells under liquid nitrogen are not specifically limited as long as they allow stable survival of the virus-infected cells and are components that do not pose any pharmacological problems to recipients.

The administration method of the recombinant herpesvirus thus prepared is not specifically limited. For example, there can be mentioned methods similar to those currently used for herpesvirus vaccines such as a method of subcutaneously injecting to the chicken individual, and a method of inoculating by making a hole during the development of the developing chicken embryos.

The amount and the timing of inoculation may the same as the conventional vaccines. For example, by inoculating subcutaneously $10^2$–$10^4$ PFU or $10^2$–$10^4$ $TCID_{50}$ to the dorsum of the chicken on the day of hatching using a 26G needle, the effect as vaccine can be expected. The recombinant herpesvirus prepared as described above functions as a vaccine against not only the pathogenic prokaryotic organisms from which the DNA molecule of the present invention was obtained but also the parent herpesvirus.

(Recombinant Poxvirus Vaccine)

In a completely similar manner to the recombinant herpesvirus etc. mentioned above, the recombinant poxvirus can be prepared as vaccine using a similar procedure. However, unlike Marek's disease virus serotype I, II, and III described as examples of recombinant herpesvirus, it is not necessary to suspend the infected cells into a culture medium containing 10% dimethyl sulfoxide (DMSO) and to store them frozen under liquid nitrogen, but the supernatant containing the recombinant poxvirus can be obtained by harvesting and homogenizing the infected cells followed by centrifugation and the like. The supernatant is generally stored lyophilized, and, as appropriate, mixed with a pharmaceutically acceptable carrier or physiological saline and then used as a vaccine, but it is possible to add a carrier or physiological saline without lyophilization and to use as a vaccine.

The method of inoculating the recombinant poxvirus, the dosage and the timing of inoculation may be the same as conventional vaccines. For example, in the case of recombinant avipoxvirus vaccine, $10^2$–$10^4$ PFu or $10^2$–$10^4$ $TCID_{50}$ is stabbed to the wing web of a chicken one week after hatching using a puncture needle.

The recombinant poxvirus thus prepared functions as a vaccine against not only the pathogenic prokaryotic organisms from which the DNA molecule of the present invention was obtained but also the parent poxvirus.

Furthermore, the recombinant vectors constructed in the construction of the recombinant virus of the present invention can be used per se as a DNA vaccine. This is a method of expressing an antigen by inoculating the purified vector directly into the eukaryotic cell individual. It can be injected or inoculated by making scratches alone or together with those that supplement expression or immunological ability, or can be introduced into a eukaryotic cell individual by the gene gun etc. and then can be used as a vaccine.

When a vector that grows in the eukaryotic cell is used, it can be introduced per se into eukaryotic cells, for example, lined cell cultures or primary cell cultures, by electroporation, the calcium phosphate method, a method that uses lipofectin, the gene gun method, and the like, and thereby the cells in which said gene has been expressed can be obtained temporarily or permanently by being integrated into the chromosome of the cell. The expressed cells per se or after purification can be used as a component vaccine.

EXAMPLES

The present invention will now be explained with reference to the Examples.

[Principles of Gene Alteration]

According to the present invention, when a potential N-glycosylation site of the gene to be expressed in a eukaryotic cell is removed, the following principles A to C were used unless otherwise specified.

A. Removal of the N-glycosylation Site

For the nucleotide sequence corresponding to the potential N-glycosylation site, Asn(N)-X-Ser(S) or Asn(N)-X-Thr (T) (X is an amino acid other than proline), the DNA sequence encoding Asn(N) was modified to a DNA sequence encoding Gln(Q).

B. Optimization of the Vicinity of the ORF Initiation Codon

Three bases at the 5' end of the ORF initiation codon ATG were modified to AAA, and a total of 6 bases comprising the initiation codon ATG and three bases located upstream thereof were changed to AAAATG. Alteration like this does not badly affect the Kosak rule or the POX rule.

C. Removal of T5NT

When T5NT that is likely to become the translational termination codon is to be expressed in poxvirus, the base sequence of the region was modified to prevent the termination of translation by taking care not to be accompanied by amino acid substitution.

D. Optimization to Codons Frequently Used in Chickens

Furthermore, optimization to codons frequently used in chickens was also performed as needed. According to the article by Nakamura et al. (1996), basically the most frequently used codon was selected, and the nucleotide sequence was modified so as to make the codon.

Reference Example 1

Alteration of the MDVgB Signal

The DNA sequences corresponding to two N-glycosylation sites present in a 186 bp (62 amino acids) signal sequence of Marek's disease virus gB protein (MDV gb signal) were modified based on the above principle of alteration A, and DNA encoding the amino acid sequence (modified MDV gb signal) was obtained. The DNA was further modified based on the above principle of alteration B and C to obtain the MDVgB signal DNA (modified MDV gb-signal) in which the 30 nucleotide sequence was modified.

The modified MDVgB signal DNA was cloned into plasmid PCR-II (Invitrogen) to construct the plasmid PCR2-MDgB-CG. There are a BamHI site on the 5'-end and an EcoRI site on the 3'-end of the modified MDVgB signal DNA in said plasmid.

Refenence Example 2

Alteration of the Rabies gG Signal

DNA encoding the rabies virus gG signal (23 amino acids) (Rabies virus glycoprotien) G(gG signal) having no N-glycosylation sites was modified based on the above principle of alteration B-D to obtain a plasmid pUC-rgG that has an modified rabies gG signal DNA (Modified rabies glycoprotien G signal).

Specific procedure to obtain this plasmid is as follows:

Thus, after annealing two synthetic DNAs as set (synthetic DNA-1:1 BN for Rabies gG and synthetic DNA-2: 1BC for Rabies gG), it was inserted into a 2665 bp BamHI-EcoRI-cleaved fragment of pUC18 to construct pUC-rgG.

Example 1

Alteration of the TTM-1 Gene from MG (1) Construction of pGTPs40KS-Ngly

There are four N-glycosylation sites in the TTM-1 portion of the amino acid sequence as set forth in SEQ ID NO: 3 of a plasmid pNZ40K-S described in International Patent Publication W097/36924 in which a MDVgB signal-encoding DNA has been ligated to the N-terminal of the antigen gene TTM-1 derived from *Mycoplasma gallisepticum*. Since there are no N-glycosylation sites in the region from the EcoRI site, the start of the TTM-1 portion, to the BglII site 83 bp downstream, the portion downstream of BglII was modified based on the above principle of alteration A to obtain a plasmid pGTPs40KS-Ngly having an modified TTM-1 gene in which the sequence downstream to the BglII site has the nucleotide sequence (TTM-1 portion of the modified pNZ-40K-S (downstream of BglI) that corresponds to the amino acid sequence. The specific procedure to obtain this plasmid is as follows:

By using a synthetic DNA as a primer, mutation was performed using PCR. The PCR used Pfu polymerase (Promega) and was performed under the usual condition using the DNA Thermal Cycler 480 of Perkin-Elmer. Twenty five to thirty cycles were performed at an annealing temperature range of 60° C. to 47° C. and after determining the optimum condition.

As a template for PCR, pGTPs4K-S having TTM-1 described in WO97/36924 and the MDVgB signal was used.

First, PCR was performed with the primer 40KG-1 and the primer 40KG-2R to obtain a 136 bp fragment.

Similarly, PCR was performed with the primer 40KG-2 and the primer 40KG-3R to obtain a 341 bp fragment.

Similarly, PCR was performed with the primer 40KG-3A and the primer 40KG-4RA to obtain 190 bp fragment.

Similarly, PCR was performed with the primer 40KG-4 and the primer 40KG-5R to obtain a 359 bp fragment.

Similarly, PCR was performed with the primer 40KG-5and the primer 40KG-6R to obtain a 218 bp fragment.

In the next PCR, using three fragments of a 136 bp RCE product of the primers 40KG-1 and 40KG-2R, a 341 bp PCR product of the primers 40KG-2 and 40KG-3R, and a 190 bp PCR product of the primers 40KG-3A and 40KG-4RA as the templates, PCR was performed in the above-mentioned condition with the primer 40KG-1 and the primer 4KG-4RA to obtain a 595 bp fragment.

Similarly, using a 359 bp PCR product of the primers 40KG-4 and 40KG-5R and a 218 bp PCR product of the primers 40KG-5 and 40KG-6R as the templates, PCR was performed in the above-mentioned condition with the primer 40KG-4 and the primer 4KG-6R to obtain a 539 bp fragment.

Furthermore, using a 595 bp PCR product of the primers 40KG-1 and 40KG-4RA and a 539 bp PCR product of the primers 40KG-4 and 40KG-6R as the templates, PCR was performed in the above-mentioned condition with the primer 40KG-1 and the primer 4KG-6R to obtain a partial fragment (1088 bp) of the modified TTM-1.

By ligating a fragment obtained by cleaving this 1088 bp fragment with BglII and SalI and a 2896 bp obtained by cleaving pGTPs40K-S described in WO97/36924 with BglII and SalI, the plasmid pGTPs40KS-Ngly having an modified TTM-1 gene in which the DNA region encoding the N-glycosylation site has been modified was constructed.

Example 2

Alteration of the mgc3 Gene Derived from MG

The amino acid sequence as set forth in SEQ ID NO: 4 encoded by the mgc3 gene (GeneBank accession No. AB023292) as set forth in SEQ ID NO: 2 has 16 N-glycosylation sites. Among the 16 sites, since a site at the most 5' upstream side is replaced with the signal sequence at a later treatment, it was excluded from the target of alteration. For the remaining 15 sites, the base sequence was modified based on the principle of alteration A to obtain the plasmid pM11BTR containing the mgc3 gene that has the nucleotide sequence (modified mgc3 gene (M11-BTR)) corresponding to the amino acid sequence (modified MG3g antigen (M11-BTR)).

The specific procedure to obtain this plasmid is as follows:

For the alteration, a synthetic DNA was used as the primer, and mutation was effected by PCR.

Since the mgc3 gene is as long as about 3 kb, it was divided into three fragments of about 1 kb in length, which were termed as the 1094 bp BKR region, the 908 bp KXR region, and the 1192 bp XGTR region. For each of these three fragments, mutation was effected, and after confirming the nucleotide sequence, they were ligated.

Using Pfu polymerase (Promega) as in Example 1, PCR was performed under the usual condition. Twenty five to thirty cycles were performed at an annealing temperature range of 60° C. to 47° C. and after determining the optimum condition. As the template for the initial alteration, pUC-MGC3 in which the mgc3 gene derived from Mycoplasma gallisepticum described in Yoshida et al. (2000) was inserted into pUC18 was used.

(1) Mutation of the BKR Region (Construction of pM11BTR)

Using pUC-MGC3 as the template, PCR was performed with the primer M11-B and the primer M11-2R to obtain a 136 bp fragment.

Using pUC-MGC3 as the template, PCR was performed with the primer M11-2 and the primer M11-3R to obtain a 92 bp fragment.

Using pUC-MGC3 as the template, PCR was performed with the primer M11-3 and the primer M11-4RB to obtain a 271 bp fragment.

Using pUC-MGC3 as the template, PCR was performed with the primer M11-4B and the primer M11-5R to obtain a 116 bp fragment.

Using pUC-MGC3 as the template, PCR was performed with the primer M11-5and the primer M11-7RA to obtain a 439 bp fragment.

Using pUC-MGC3 as the template, PCR was performed with the primer M11-7 and the primer M11-2KR to obtain a 201 bp fragment.

In the next PCR, using a 136 bp PCR product of the primer M11-B and the primer M11-2R and a 92 bp PCR product of the primer M11-2 and the primer M11-3R as the templates, PCR was performed with the primer M11-B and the primer M11-3R to obtain a 199 bp fragment.

Similarly, using a 271 bp PCR product of the primer M11-3 and the primer M11-4RB and a 116 bp PCR product of the primer M11-4B and the primer M11-5R as the templates, PCR was performed with the primer M11-3 and the primer M11-5R to obtain a 344 bp fragment.

Similarly, using a 439 bp PCR product of the primer M11-5A and the primer M11-7RA and a 201 bp PCR product of the primer M11-7 and the primer M11-KR as the templates, PCR was performed with the primer M11-5A and the primer M11-KR to obtain a 610 bp fragment.

Using these three PCR products, a PCR product (199 bp) of the primer M11-B and the primer M11-3R, and a PCR product (361 bp) of the primer M11-3 and the primer M11-5R, and a PCR product (610 bp) of the primer M11-5A and M11-KR as the templates, PCR was performed with the primer M11-B and the primer M11 -KR to obtain a 1094 bp fragment. A 1070 bp fragment obtained by cleaving this PCR product (1094 bp) 10 of the primers M11-B and M11-KR with EcoRI and KpnI was inserted into a 2678 bp fragment of the plasmid pUC18 cleaved with EcoRI and KpnI to construct pM11BKR.

After analyzing the nucleotide sequence of this pM11BKR, a sequence different from the mgc3 gene (GeneBank accession No. AB023292) registered in GeneBank was found. Furthermore, the sequence of the original plasmid pUC-MGC3 was compared to confirm that it was not an error in PCR. As a result, it was confirmed that G at position 308 of SEQ ID NO: 2, a sequence registered at GeneBank, is T, G at position 311 is C, C at position 561 is G, and G at position 749 is T. It was demonstrated that due to an error in the base at position 561, the amino acid sequence encoded in this region is not N-Asn(N)-Gln(Q)-Thr(T) corresponding to the N-glycosylation site but Gln (Q)-Gln(Q)-Thr(T).

(2) Mutation of the KXR Region (construction of pM11KXR)

Using pUC-MGC3 as the template, PCR was performed with the primer M11-K and the primer M11-8R to obtain a 151 bp fragment.

Using pUC-MGC3 as the template, PCR was performed with the primer M11-8 and the primer M11-10R to obtain a 109 bp fragment.

Using pUC-MGC3 as the template, PCR was performed with the primer M11-10 and the primer M11-12RA to obtain a 416 bp fragment.

Using pUC-MGC3 as the template, PCR was performed with the primer M11-12A and the primer M11-XR to obtain a 350 bp fragment.

In the next PCR, using a 109 bp PCR product of the primer M11-8 and the primer M11-10R and a 416 bp PCR product of the primer M11-10 and the primer M11-12RA as the templates, PCR was performed with the primer M11-8 and the primer M11-12RA to obtain a 487 bp fragment.

Furthermore, using a 151 bp PCR product of the primer M11-K and the primer M11-8R and a 487 bp PCR product of the primer M11-8 and the primer M11-12RA as the templates, PCR was performed with the primer M11-K and the primer M11-12RA to obtain a 596 bp fragment.

Using the above two PCR products, a 596 bp PCR product of the primer M11-K and the primer M11-12RA and a 350 bp PCR product of the primer M11-12A and the primer M11-XR as the templates, PCR was performed with the primer M11-K and the primer M11-XR to obtain a 908 bp fragment.

A 885 bp fragment obtained by cleaving this PCR product (908 bp) of the primer M11-K and the primer M11-XR with KpnI and XbaI was inserted into the plasmid pUC18 cleaved with KpnI and XbaI to construct pM11KXR.

After analyzing the nucleotide sequence of this pM11KXR, a sequence different from the mgc3 gene (GeneBank accession No. AB023292) registered in GeneBank was found. Furthermore, the sequence of the original plasmid pUC-MGC3 was compared to confirm that it was not an error in PCR. As a result, it was confirmed that G at position 1279 of SEQ ID NO: 2, a sequence registered at GeneBank, is A, T at position 1729 is G, and C at position 1732 is G.

(3) Mutation of the XGTR Region (construction of pM11XGTR)

Using pUC-MGC3 as the template, PCR was performed with the primer M11-XA and the primer M11-13RA to obtain a 238 bp fragment.

Using pUC-MGC3 as the template, PCR was performed with the primer M11-13A and the primer M11-14RA to obtain a 266 bp fragment.

Using pUC-MGC3 as the template, PCR was performed with the primer M11-14A and the primer M11-15RA to obtain a 168 bp fragment.

Using pUC-MGC3 as the template, PCR was performed with the primer M11-15A and the primer M11-16RA to obtain a 123 bp fragment.

Using pUC-MGC3 as the template, PCR was performed with the primer M11-16A and the primer M11-GTR to obtain a 556 bp fragment.

In the next PCR, using a 238 bp PCR product of the primer M11-XA and the primer M11-13RA and a 266 bp PCR product of the primer M11-13A and the primer M11-14RA as the templates, PCR was performed with the primer M11-XA and the primer M11-14RA to obtain a 463 bp fragment.

Furthermore, using a 168 bp PCR product of the primer M11-14A and the primer M11-15RA and a 123 bp PCR product of the primer M11-15A and the primer M11-16RA as the templates, PCR was performed with the primer M11-14A and the primer M11-16RA to obtain a 253 bp fragment.

Using the above three fragments of a 463 bp PCR product of the primer M11-XA and the primer M11-14RA, a 253 bp PCR product of the primer M11-14A and the primer M11-16RA, and a 556 bp PCR product of the primer M11-16A and the primer M11-GTR as the templates, PCR was performed with the primer M11-XA and the primer M11-GTR to obtain a 1192 bp fragment.

A 1174 bp fragment obtained by cleaving this PCR product (1192 bp) of the primer M11XA and the primer M11-GTR with XbaI and SalI was inserted into a 2680 bp fragment of the plasmid pUC18 cleaved with XbaI and SalI to construct pM11XGTR.

After analyzing the nucleotide sequence of this pM11XGTR, a sequence different from the mgc3 gene (GeneBank accession No. AB023292) registered in GeneBank was found. Furthermore, the sequence of the original plasmid pUC-MGC3 was compared to confirm that it was not an error in PCR. As a result, it was confirmed that G at position 3113 of SEQ ID NO: 2, a sequence registered at GeneBank, is C.

(4) Construction of the Plasmid pM11BTR Containing the Sugar Chain-Removed Full-Length mgc3

A 885 bp fragment prepared by cleaving pM11KXR with KpnI and XbaI and a 1174 bp fragment prepared by cleaving pM11GTR with XbaI and SalI were ligated to a 3723 bp fragment prepared by cleaving pM11BKR with KpnI and SalI thereby to construct pM11BTR having the modified mgc3 gene in which the DNA region encoding a N-glycosylation site was modified.

Example 3

Preparation of Vectors for Recombinant Fowlpox Virus (1) Construction of pUCSfi-H-S A 2676 bp fragment obtained by cleaving, with HindIII and SalI, pUC18XG described in International Patent Publication WO99/18215 in which the restriction sites of pUC18 were modified and an annealing product of a 5'-end-phosphorylated linker H'-S-H-S-P-S1 and a linker H'-S-H-S-P-S2 were ligated to construct pUCSfi-H-S.

(2) Construction of pGHPs

Three fragments, a 2661 bp fragment obtained by cleaving pUCSfi-H-S with HindIII and EcoRI, an annealing product of a 5'-end-phosphorylated linker S-B-E1 and a linker S-B-E2, and a 137 bp fragment obtained by cleaving, with HindIII and SalI, the plasmid described in International Patent Publication WO97/36924 containing the poxvirus late and early promoter, were ligated to construct a plasmid pGHPs.

(3) Construction of pGTPs40KS(CG1)

A plasmid PCR2-MDgB-CG having the MDVgB signal DNA modified in Reference Example 1 was cleaved with BamHI and EcoRI to obtain a 189 bp fragment.

pGTPs40K-S having the MDVgB signal DNA described in International Patent Publication WO97/36924 and the TTM-1 gene were cleaved with BamHI and EcoT22I to collect a 3402 bp DNA fragment. Similarly, pGTPs-40K-S was cleaved with EcoRI and EcotT22I to collect a 557 bp DNA fragment. The three fragments thus obtained were ligated to construct a plasmid pGTPs40KS(CG1).

(4) Construction of pGTPs40K-G-CS

A 3067 bp fragment obtained by cleaving the plasmid pGTPs40K-Ngly having the modified TTM-1 gene obtained in Example 1 with BglII and SalI and a 1082 bp fragment obtained by cleaving pGTPs40KS(CG1) obtained in the above (3) with BglII and SalI were ligated to construct a plasmid pGTPs40K-G-CS.

(5) Construction of pNZ1829R/40K-G-CS

A 9217 bp fragment obtained by cleaving a plasmid pNZ1829R described in WO97/36924 containing a sequence for homologous recombination of FPV, the late promoter and the early promoter of pox, and a marker gene, lacZ gene, with BamHI and SalI, and a 1347 bp fragment obtained by cleaving pGTPs40K-G-CS obtained in the above (4) with BamHI and SalI were ligated to construct a plasmid pNZ1829R/40K-G-CS having an modified TTM-1 gene in which the modified MDVgB signal DNA was connected in frame and the lacZ gene as a marker gene.

(6) Construction of pNZ1829R/40K-G-CS(dl-lacZ)

A 7013 bp fragment obtained by cleaving this plasmid pNZ1829R/40K-G-CS with SmaI and SfiI was treated with T4 polymerase, blunted, and the fragment obtained was subjected to self-ligation to construct a plasmid pNZ1829R/40K-G-CS (dl-lacZ) in which the lacZ gene was deleted from the plasmid pNZ1829R/40K-G-CS. By sequencing, the nucleotide sequence of the blunted portion was confirmed.

Example 4

Construction of Vectors for Recombinant Fowlpox Virus (1) Construction of pGHPs40KCS-G A 1347 bp fragment obtained by cleaving pGTPs40K-G-CS constructed in Example 3(4) with BamHI and SalI and a 2791 bp fragment obtained by cleaving pGHPs constructed in Example 3(2) with BamHI and SalI were ligated to construct pGHPs40KCS-G.

(2) Construction of pNZ29RMG40KM11CS-G

A 3129 bp fragment obtained by cleaving pM11BTR having the modified mgc3 gene constructed in Example 2(4) with EcoRI and SalI, a 297 bp fragment obtained by cleaving pGHPs40KCS-G obtained in the above (1) with EcoRI and SfiI, and a 6985 bp fragment obtained by cleaving pNZ1829R/40K-G-CS constructed in Example 3(5) with SfiI and SalI were ligated to construct a plasmid pNZ29RMG40KM11CS-G having the modified MDVgB signal DNA, the modified TTM-1 gene, and the modified mgc3 gene.

Example 5

Construction of a Vector pNZ29RMG40KM11CS-G2 for Recombinant Fowlpox Virus

In Example 4, the modified mgc3 gene has been inserted in the constructed pNZ29RMG40KM11CS-G. In order to return the site that, inherently, is not a N-glycosylation site (corresponding to base at position 561 in SEQ ID NO: 2) of the gene to the original base G, this part was further modified, and a plasmid pNZ29RMG40KM11CS-G2 having the re-modified mgc3 gene was obtained.

The specific procedure used for re-altering mgc3 is as follows:

Using pNZ29RMG40KM11CS-G constructed in Example 4(2) as the template, PCR was performed with the primer M11-Sfi and the primer M11-5RB in the condition described in Example 1 to obtain a 836 bp fragment.

Using pNZ29RMG40KM11CS-G constructed in Example 4(2) as the template, PCR was performed with the primer M11-5C and the primer M11-KRA in a similar condition to obtain a 618 bp fragment.

Using these two PCR products as the templates, PCR was performed with the primer M11-Sfi and the primer M11-KRA to obtain a 1400 bp fragment. A 1368 bp fragment obtained by cleaving this 1400 bp PCR product with SfiI and KpnI and a 9032 bp fragment obtained by cleaving pNZ29RMG40KM11CS-G constructed in Example 4(2) with SfiI and KpnI were ligated to construct a plasmid pNZ29RMG40KM11CS-G2 having the modified MDVgB signal DNA, the modified TTM-1 gene, and the re-modified mgc3 gene.

By sequencing the modified part, the nucleotide sequence was confirmed.

Example 6

Construction of Vectors for Recombinant HVT (1) Construction of pGIPec40KS

A 3278 bp fragment obtained by cleaving the plasmid pGIPec described in Japanese Unexamined Patent Publication (Kokai) No. 2001-188 having the Pec promoter and the polyA signal (Yanagida et al., 1993) of UL46h, UL47h and UL49h with BamHI and SalI and a 1344 bp fragment obtained by cleaving pGTPs40K-G-CS constructed in Example 3(4) with BamHI and SalI fragments were ligated to construct a plasmid pGIPec40KS.

(2) Construction of p45/46MG40KS

To the SfiI site of the plasmid pNZ45/46Sfi described in International Patent Publication WO99/18215 having the homologous recombination site of UL44-UL46 of HVT, a BglI fragment (1969 bp) of pGIPec40KS obtained in the above (1) was inserted to construct a plasmid p45/46MG40KS.

(3) Construction of pGICMV(−)

Using pGIPec described in Japanese Unexamined Patent Publication (Kokai) No. 2001-188 as the template, PCR was performed in the condition created in Example 1 with the primer pCMV-1 and the primer pPeclR to obtain a 293 bp fragment.

Using pBK-CMV (Stratagene) as the template, PCR was performed in a similar condition with the primer pCMV-ol and the primer CMV-R1 to obtain a 341 bp fragment.

Using the two PCR products obtained as the templates, PCR was performed with the primer pCMV-1 and the primer pCMV-R1to obtain a 604 bp fragment.

A 589 bp fragment obtained by cleaving this 604 fragment with PstI and XbaI and a 2765 bp fragment obtained by cleaving pGIPec with PstI and XbaI were ligated to construct pGICMV(−).

(4) Construction of pGHMCSpolyASfi

Using the plasmid pGIMCSpolyASfi described in International Patent Publication WO99/18215 having the polyA signal of UL46h, UL47h and UL49h and a multiple cloning site as the template, PCR was performed with the primer pGHP-F and the primer pGHP-R to obtain a 149 bp fragment.

A 138 bp fragment obtained by cleaving this 149 bp fragment with EcoRI and HindIII and a 2635 bp fragment obtained by cleaving pGIMCSpolyASfi with EcoRI and HindIII were ligated to obtain pGHMCSpolyASfi.

(5) Construction of pGHCMV(−)

A 2765 bp fragment obtained by cleaving pGHMCSpolyASfi obtained in the above (4) with PstI and XbaI and a 589 bp fragment obtained by cleaving pGICMV(−) obtained in the above (3) with PstI and XbaI were ligated to construct pGHCMV(−).

(6) Construction of pHCMV(−)

A 3294 bp fragment obtained by cleaving pGHCMV(−) obtained in the above (5) with EcoRI and SalI and an annealing product of 5'-end-phosphorylated Linker 1 and a Linker 2 were ligated to construct a plasmid pHCMV(−) in which the polyA signal of UL46h, UL47h, and UL49h of MDV-1 was deleted in pGHCMV(−).

(7) Construction of pHCMV-M11 (CSG2)

A 3275 bp fragment obtained by cleaving pHCMV(−) obtained in the above (6) with BamHI and SalI and a 3318 bp fragment obtained by cleaving pNZ29RMG40KM11CS-G2 obtained in Example 5 with BamHI and SalI were ligated to construct a plasmid pHCMV-M11 (CSG2).

(8) Construction of pBAc

A 1515 bp fragment obtained by cleaving a plasmid pLUC-bac having the chicken beta-actin promoter described in Japanese Unexamined Patent Publication (Kokai) No. 2001-188 with PstI and XbaI and a 2765 bp fragment obtained by cleaving pGIMCSpolyASfi described in International Patent Publication WO99/18215 with PstI and XbaI were ligated to construct a plasmid pBAc.

(9) Construction of pBAc (dHS)

A 4268 bp fragment obtained by cleaving a plasmid pBAc obtained in the above (8) with XbaI after partially cleaving with HindIII and an annealing product of 5'-end-phosphorylated Linker 3 (SEQ ID NO: 72) and a Linker 4 (SEQ ID NO: 73) were ligated to construct a plasmid pBAc(dHS).

(10) Construction of pGIBacpA2nd

Using pBK-CMV (Stratagene) as the template, PCR was performed with the primer PolyA-SfiF2 and the primer PolyA-SalKpn to obtain a 313 bp fragment having the PolyA signal of SV40. A 297 bp fragment obtained by cleaving this 313 bp fragment with SfiI and Kpn and a 4222 bp fragment obtained by cleaving pBAc(dHS) obtained in the above (9) with SfiI and KpnI were ligated to construct pGIBacpA2nd.

(11) Construction of pGIBac40KS2nd

Using pGTPs40K-S described in International Patent Publication WO97/36924 as the template, PCR was performed with the primer 40KS-B and 40KG-6R to obtain a 1359 bp fragment. A 1345 bp fragment obtained by cleaving this 1359 bp fragment with BamHI and SalI and a 4222 bp fragment obtained by cleaving pGIBacpA2nd obtained in the above (10) with BamHI and SalI were ligated to construct a plasmid pGIBac40KS2nd.

(12) Construction of p45/46Bac40KS+2nd

A 3169 bp fragment obtained by cleaving pGIBac40KS2nd obtained in the above (11) with BglI was inserted into the SfiI site of pNZ45/46Sfi having the UL44 to UL46 region (HVT-U44-46) of HVT described in W097/36924 to construct a plasmid p45/46Bac40KS+2nd having the TTM-1 gene.

(13) Construction of p45/46Bac40KS-CMVM11

A 3940 bp fragment obtained by cleaving pHCMV-M11 (CSG2) obtained in the above (7) with BglI was inserted into the SfiI site of p45/46Bac40KS+2nd obtained in the above (12) to construct a plasmid p45/46Bac40KS-CMVM11 having the mgc3 gene.

(14) Construction of p45/46Pec40KS+2nd

A 561 bp fragment obtained by cleaving pGIPec40KS obtained in the above (1) with PstI and BamHI, a 3520 bp fragment obtained by cleaving p45/46Bac40KS+2nd obtained in the above (12) with BamHI and HindIII, and a 3613 bp fragment obtained by cleaving the same plasmid with PstI and HindIII were ligated to construct a plasmid p45/46Pec40KS+2nd having the modified MDVgB signal DNA and the modified TTM-1 gene.

(15) Construction of pNZ45/46BacpA2nd

A 1866 bp fragment obtained by cleaving pGIBacA2nd obtained in the above (11) with BglI was inserted into the SfiI site of pNZ45/46Sfi described in WO99/18215 to construct pNZ45/46BacpA2nd.

(16) Construction of pNZ45/46Bac40KpA+2nd

Using pUTTM-1 described in U.S. Pat. No. 5,489,430 as the template, PCR was performed with primer pMG40K-1 and the primer 40KG-6R to obtain a 1259 fragment. A 1237 bp fragment obtained by cleaving this 1259 bp fragment with BamHI and SalI and a 7317 bp fragment obtained by cleaving pNZ45/46BacpA2nd obtained in the above (15) with BamHI and SalI were ligated to construct a plasmid pNZ45/46Bac40KpA+2nd.

(17) p45/46Bac40K-CMVM11

A 3940 bp fragment obtained by cleaving pHCMV-M11 (CSG2) obtained in the above (7) with BglI was inserted into the SfiI site of pNZ45/46Bac40KpA2nd obtained in the above (16) to construct a plasmid p45/46Bac40K-CMVM11 having the modified MDVgB signal DNA, the modified TTM-1 gene, and the modified mgc3 gene.

Example 7

Construction of Vectors for Recombinant FowlPox Virus (1) Construction of pNZ29R/40KMGC3

A 1345 bp fragment obtained by cleaving pGIBac40KS2nd constructed in Example 6(11) with BamHI and SalI, a 1333 bp fragment obtained by cleaving pNZ29RMG40KM11CS-G2 constructed in Example 5 with EcoT22I and BamHI, and a 7722 bp fragment obtained by cleaving the same plasmid with EcoT22I and SalI were ligated to construct a plasmid pNZ29R/40KMGC3 that is a vector for recombinant fowlpox virus having the modified MDVgB signal DNA, the modified TTM-1 gene, and the re-modified mgc3 gene.

(2) Construction of pNZ29RMG40KSM11CS-G2

A 1440 bp fragment obtained by cleaving pGTPs40KS-Ngly constructed in Example 1 with HindIII and SalI, a 1237 bp fragment obtained by cleaving pNZ29RMG40KM11CS-G2 constructed in Example 5 with HindIII and EcoT22I, and a 7722 bp fragment obtained by cleaving the same plasmid with EcoT22I and SalI were ligated to construct a plasmid pNZ29RMG40KSM11CS-G2 that is a vector for recombinant fowlpox virus having the modified MDVgB signal DNA, the modified TTM-1 gene, and the re-modified mgc3 gene.

(3) Construction of pGHPs-rgG

A 75 bp fragment obtained by cleaving pUC-rgG constructed in Reference Example 2 with BamHI and EcoRI and a 2756 bp fragment obtained by cleaving pGHPs40KCS-G constructed in Example 4 with BamHI and EcoRI were ligated to construct a plasmid pGHPs-rgG.

(4) Construction of pNZ29RMG40KSM11(rgG)CS-G2

A 3129 bp fragment obtained by further cleaving, with EcoRI, a 3418 bp fragment obtained by cleaving pNZ29R/40KMGC3 obtained in the above (1) with SfiI and SalI, a 6982 bp fragment obtained by cleaving the same pNZ29R/40KMGC3 with SfiI and SalI, and a 176 bp fragment obtained by cleaving pGHPs-rgG constructed in the above (3) with SfiI and EcoRI were ligated to construct a plasmid pNZ29RMG40KSM11(rgG)CS-G2 having that is a vector for recombinant fowlpox virus having the modified rgG gene, the modified TTM-1 gene, and the re-modified mgc3 gene.

Example 8

Purification of Recombinant Fowlpox Virus

To a monolayer of CEFs, the BLEN strain (FP-Blen Select Laboratories) that is a live vaccine for fowl pox was infected at a M.O.I. of 0.1. Three hours later, these cells were trypsinized to make a cell. suspension. The cells ($2\times10^7$ cells) in this suspension and 10 $\mu$g of one of the vectors for recombinant fowlpox virus shown in Table 1 constructed in the above Examples were mixed, and the mixture was suspended into Saline G (0.14 M NaCl, 0.2 mM KCl, 1.1 mM hydrogen disodium phosphate, 1.5 mM hydrogen potassium phosphate, 0.5 mM magnesium chloride hexahydrate, 0.011% glucose), which was then subjected to electroporation at a condition of 3.0 $KVcm^{-1}$ and 0.4 msec at room temperature using the Gene Pulser (Bio-Rad). Cells into which the vector for recombinant fowlpox virus had been introduced were then cultured for 72–120 hours, freeze-thawed 3 times, and the cells containing recombinant fowlpox virus were collected. The relationship between the vector for recombinant fowlpox virus and the name of the recombinant fowlpox virus obtained from the vector is shown in Table 1.

TABLE 1

The relationship between the recombinant fowlpox virus and the recombinant vector

| Vector for recombinant fowlpox virus | recombinant fowlpox virus |
|---|---|
| pNZ1829R/40K-S (dl-lacZ) | rFPV-B/MG40- |
| pNZ29RMG40KM11CS-G | rFPV-B/MG40/M11 |
| pNZ1829R/40K-G-CS | rFPV-B/MG40-S |
| pNZ29R/40KMGC3 | rFPV-B/MG-1 |
| pNZ29RMG40KS(-G)M11CS-G2 | rFPV-B/MG-2 |
| pNZ29RMG40KSM11(rgG)CS-G2 | rFPV-B/MG-3 |

The recovered virus was purified by the Black Plaque Assay (BPA).

The solution of the recovered virus was infected to the monolayer of CEFs, on which agar containing the growth medium was overlaid. After confirming virus plaques 2–3 days later, each virus plaque was collected individually with the agar on it with a Pasteur pipet etc., suspended in the growth medium, and stored. On the other hand, agar was removed from CEFs having the remaining plaques, which was then fixed in cold methanol etc. Antiserum (anti-TTMG-1 antiserum) obtained by immunizing rabbits with the TTMG-1 protein that was expressed in Escherichia coli was diluted about 500-fold in Dulbecco's phosphate buffered saline (Dainippon Pharmaceutical; hereinafter referred to as PBS(−)) which is usually used for cell culture and includes no magnesium ion, and was reacted to the plaques at 22–25° C. for 2 hours. The antibody that was not bound was washed three times in 3% non-fat dried milk in PBS(−), and then, biontinylated anti-rabbit antibody (goat, Biosource) was reacted to the plaque at 22–25° C. for 2 hours.

After the reaction was over the antibody was washed out by PBS(−), avidin-biotin-alkaline phosphatase complex (Vector Laboratories) was reacted. After rinsing off the unreacted avidin-biotin-alkaline phosphatase complex in PBS(−), plaques were developed with the substrate for alkaline phosphatase, BCIP/NBT (Roche), a which creates dark blue or black precipitate. Using this BPA, viral suspensions corresponding to positive plaques were re-infected to CEFs and similar procedures were repeated for 3–4 times until all plaques became positive with BPA. The gene structure of recombinants was confirmed by Southern hybridization and the sequencing of the DNA sequence at the junction.

Example 9

Purification of Recombinant HVT

According to the method of Morgan et al. (1990), HVT-DNA was recovered. The specific method of collection is as follows:

About $10^5$ PFU of the HVT FC126 strain (ATCC VR-584B) was infected to about $3\times10^7$ CEFS. After culturing for 2–3 days, 4 ml of the lysis buffer (0.5% SDS, 10 mM Tris (pH 8.0), 100 mM NaCl, 1 mM EDTA, 200 μg/ml Proteinase K) was added thereto, and incubated at 37° C. for 4 hours, phenol-extracted, and precipitated with ethanol to recover HVT-DNA.

The vectors for recombinant HVTs shown in Table 2 obtained in the above Examples were cleaved with an appropriate restriction enzyme into linearized at the site which is located on neither the homologous region to HVT genome nor the foreign gene(s).

About $3\times10^6$ CEFs collected by trypsinization were suspended in saline G (0.14 M NaCl, 0.2 mM KCl, 1.1 mM hydrogen disodium phosphate, 1.5 mM hydrogen potassium phosphate, 0.5 mM magnesium chloride hexahydrate, 0.011% glucose). 10–30 μg of the previously prepared HVT-DNA and 10–30 g of the linearized vector for recombination were introduced into the cells by electroporation at a condition of 0.5 $KVcm^{-1}$ and 0.4 msec at room temperature using Gene Pulser (Bio-Rad). This cell suspension was plated on a 6-cm culture dish, to which the growth medium was added and cultured for 5–7 days. The infected cells which contained recombinant HVTs were harvested. The recombinant HVT was purified by the limiting dilution method. The specific method of purification is as follows:

About $2\times10^6$ CEFs together with the serially diluted viral solutions were plated on 96-well plates. After culturing for 3–5 days when plaques appeared, replica was made. From one of the plates, using a similar method to the BPA method in Example 8, recombinant HVTs that expressed the TTM-1 gene were selected. In a similar manner to recombinant fowlpox virus, the viral solutions of the replica corresponding to positive plaques were re-infected to CEFs, and similar procedures were repeated for 3–4 times until all plaques became positive by the BPA method.

The relationship between the vectors for HVT and the recombinant HVTs obtained from the vector is shown in Table 2.

TABLE 2

The relationship between the name of the recombinant HVT and the recombinant vector

| Vector for recombinant HVT | recombinant HVT |
|---|---|
| p45/46MG40KS | rHVT/PecMG40KS |
| p45/46Bac40KS − CMVM11 | rHVT/Bac40KS − CMVM11 |
| p45/46Pec40KpA + 2nd | rHVT/PecMG40KS + 2nd |
| p45/46Bac40K − CMVM11 | rHVT/Bac40K − CMVM11 |

The gene structure of recombinants was confirmed by Southern hybridization and the sequencing of the DNA sequence at the junction.

Example 10

Confirmation of the Protein Expressed from the Recombinants (The BPA Method)

It has already been confirmed by the BPA method in each Example that all of the recombinant fowlpox viruses and the recombinant HVTs obtained in Examples 8 and 9 have the TTM-1 gene or the modified TTM-1 gene and express the TTMG-1 antigen.

For recombinant viruses having the mgc3 gene or the modified mgc3 gene obtained in Examples 8 and 9, rFPV-B/MG40/M11, rFPV-B/MG-1, rFPV-B/MG-2, rFPV-B/MG-3, rHVT/Bac40KS-CMVM11, and rHVT/Bac40K-CMVM11, the BPA method was performed as in Example 8 using mouse monoclonal antibody Mab 35A6 raised against the MGC3 antigen prepared by Yoshida et al. (2000) (however, it differs in that the second antibody is a biotinylated anti-mouse antibody (goat, Biosource)) to confirm the expression of the MGC3 antigen.

Example 11

Confirmation of the Protein Expressed from the Recombinants (The Western Blotting Method)

The molecular weight of recombinant virus was determined using the Western blotting method. The procedure by the Western blotting method is as follows:

The monolayer of CEFs infected with recombinant virus was solubilized in the SDS-GEL loading buffer. For some samples, sugar chains were digested as they are using sugar chain-digesting enzymes, endoglycosidase H (Endo H; Roche) and PNGase F (Endo F; Roche). These samples were subjected to SDS-PAGE electrophoresis under the normal denaturing reduced condition. Protein was transferred from the gel to the PVDF membrane (Immobilon-P, Millipore). The PVDF membrane was incubated with the anti-TTMG-1 antiserum or Mab 35A6 described in Example 10, and rinsed in Tris buffered saline with Tween 20 (T-TBS: 0.1 M Tris-Cl (pH 7.5), 0.9% NaCl, 0.1% Tween 20 (manufactured by Sigma-Aldrich)). The membrane was incubated with a second antibody (anti-rabbit (goat) for anti-TTM-1 antiserum, and anti-mouse (goat) for Mab 35A6). After rinsing with T-TBS, it was reacted with the avidin-biotin-alkaline phosphatase complex (vector Laboratories). By rinsing off the unreacted avidin-biotin-alkaline phosphatase complex in T-TBS, protein bands were observed after development with the substrate for alkaline phosphatase, BCIP/NBT (Roche), which creates dark blue or black precipitate.

It was confirmed by the Western blotting method that the recombinant fowlpox virus rFPV-B/MG40/M11 (Lane 3) obtained in Example 8 expresses the TTMG-1 antigen (FIG. 1). As the control, the parent fowlpox virus BLEN strain (Lane 1), and a recombinant fowlpox virus in which the MDVgB signal was connected in frame to the TTMG-1 antigen having a sugar chain described in International Patent Publication WO97/36924, 40K-S (Lane 2), and the recombinant fowlpox virus recFPV-MGC3 (Lane 4) that expresses the MGC3 antigen reported by Yoshida et al. (2000) were used.

As shown in FIG. 1, 40K-S (Lane 2) that expresses the TTMG-1 antigen having a N-glycosylation site expressed an about 60 kd TTMG-1 antigen. On the other hand, rFPV-B/MG40/M11 (Lane 3) that expresses the TTMG-1 antigen in which the N-glycosylation site was modified expressed an about 50 kd TTMG-1 antigen. This is consistent with the value of 48.9 kd predicted from the amino acid sequence in which the MDVgB signal was added to the N-glycosylation site-modified TTM-1. In the negative control of the parent virus (Lane 1) that did not express TTMG-1 antigen and recFPV-MGC3 (Lane 4) did not exhibit any specific bands.

Figure 2:
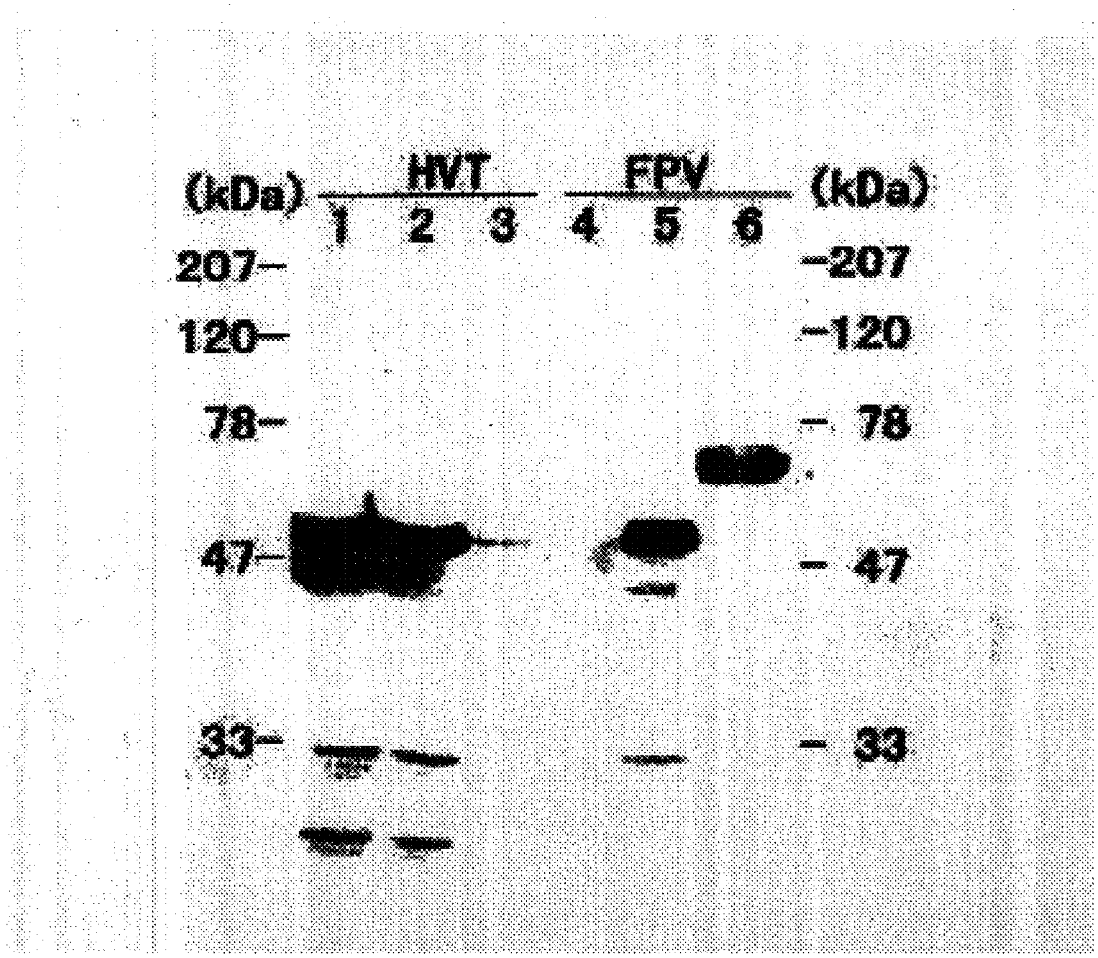
FIG. 2 is a Western blot that compares the molecular weight detected using anti-TTMG-1 antiserum of the non-N-glycosylated TTMG-1 fusion protein (lane 5) expressed from the FPV containing the fused DNA of a DNA encoding the modified TTMG-1 antigen and a DNA encoding the signal sequence MDVgB, the non-N-glycosylated TTMG-1 fusion protein (lane 1 and 2) expressed from the HVT containing said fused DNA, and the N-glycosylated TTMG-1 fusion protein (lane 6) expressed from the FPV containing the unmodified DNA. In this figure, lane 4 indicates the result from FPV (negative control) containing no antigen gene and lane 3 indicates the result of the antigen protein NDV that cannot be detected with the above anti-serum.

It was confirmed by the Western blotting method that the recombinant fowlpox virus rFPV-B/MG40-S (Lane 5)

obtained in Example 8 and the recombinant HVT rHVT/PecMG40KS (Lanes 1 & 2) obtained in Example 9 expressed the TTMG-1 antigen (FIG. 2). As the control, rHVT HF-PecHNF (Lane 3) that expresses the HN and F antigen of NDV described in Japanese Unexamined Patent Publication (Kokai) No. 2001-188, the parent fowlpox virus BLEN strain (Lane 4), 40K-S (Lane 5) described in International Patent Publication WO97/36924 were used. Lanes 1 and 2 are HVT having the-same structure except that their clones are only different. rFPV-B/MG40-S (Lane 5) that expresses the N-glycosylation site-modified TTMG-1 antigen and rHVT/PecMG40KS (Lanes 1 & 2) expressed about 50 kd TTMG-1 antigen as did rFPV-B/MG40/M11 (Lane 3) in FIG. 1. This was consistent with the value of 48.9 kd predicted from the amino acid sequence in which the MDVgB signal was added to the N-glycosylation site-modified modified TTM-1. On the other hand, 40K-S (lane 6) that expresses the TTMG-1 antigen having a sugar chain is the same virus as in Lane 2 in FIG. 1, but the-former expressed about 60 kd TTMG-1 antigen. In HF-PecHNF (Lane 3) that expresses NDV, there appears to be a band at about 50 kd, but this was confirmed to be a contamination from Lane 2 in another experiment. In the negative control of the FPV parent strain (Lane 4), no bands were seen. Thus, it was demonstrated that FPV and HVT that express a fusion protein comprised of the N-glycosylation site-modified TTM-1 and the MDVgB signal were not N-glycosylated.

Figure 3:
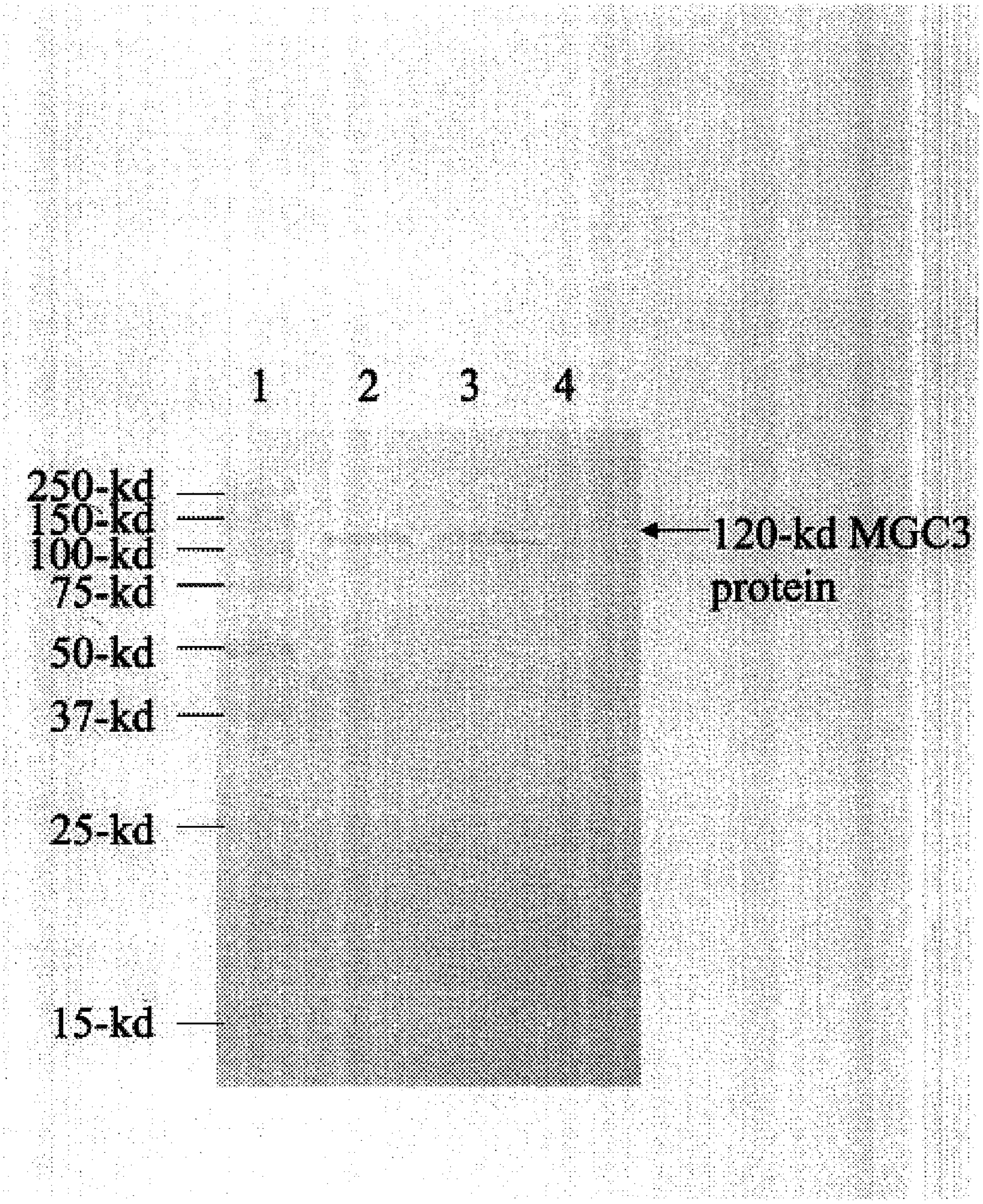
FIG. 3 is a Western blot that shows that the molecular weight of the non-N-glycosylated fusion protein expressed from the FPV containing the fusion of a DNA encoding the modified MGC3 antigen and a DNA encoding the signal sequence MDVgB is 120 kd. It has been separately confirmed that the molecular weight of the N-glycosylated MGC3 antigen expressed from the unmodified mgc3 gene is 140 kd. In this figure, lane 1 indicates the molecular weight standard and lane 4 indicates the result from the virus containing no antigen gene.

It was confirmed by the Western blotting method that the recombinant fowlpox virus rFPV-B/MG-1 (Lanes 2 & 3) obtained in Example 8 expresses the MGC3 antigen (FIG. 3). As the negative control, the parent fowlpox virus BLEN strain (Lane 4) was used. According to Yoshida et al. (2000), the size of the fusion protein, expressed by recFPV-MGC3-S, of the MDVgB signal having a N-glycosylation site and MGC3 is 145 kd. The size of the fusion protein of the N-glycosylation site-modified MGC3 antigen that is a gene product of mgc3 of FPV-B/MG-1 obtained in the above Example and the MDVgB signal is 120 kd (Lane 2 & 3). This is consistent with the molecular weight when a sugar chain estimated from the amino acid sequence was not added (not N-glycosylated). This size of 120 kd of the MGC3 antigen is consistent with the fact by Yoshida et al. (2000) that the size of the MGC3 antigen in which the MGC3 antigen of recFPV-MGC3-S was treated with endoglycosidase H and PNGase F and the sugar chain was removed is 120 kd.

Figure 4:
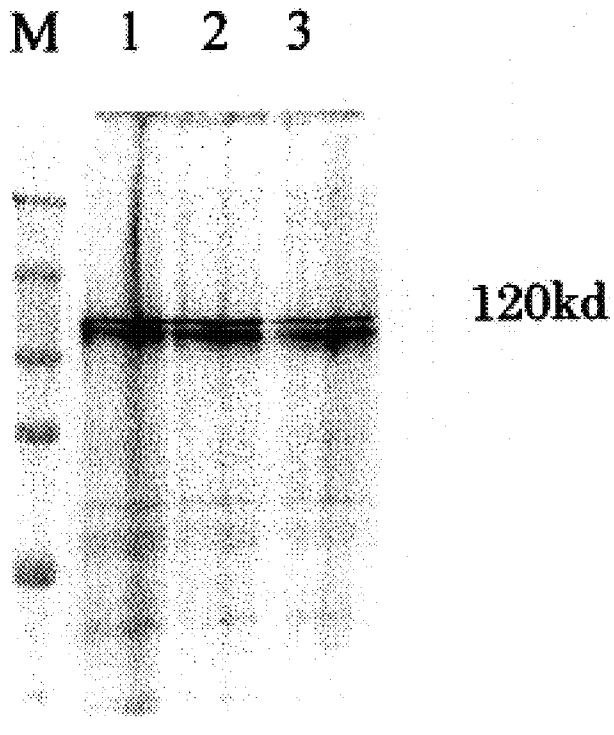
FIG. 4 is a Western blot that shows that the treatment of the non-N-glycosylated MGC3 antigen (molecular weight 120 kd) expressed from the virus into which an modified mgc3 gene was introduced with a sugar chain-cleaving enzyme endoglycosidase or PNGase F does not change (reduce) the molecular weight.

Furthermore, for the recombinant fowlpox virus rFPV-B/MG-1 (Lane 1–3) obtained in Example 8, the expressed protein was treated with PNGase F (Lane 1) and endoglycosidase H (Lane 2), and then subjected to Western blotting using Mab 35A6 (FIG. 4). As a result, it was demonstrated, that despite the treatment with endoglycosidase H or PNGase F, it was 120 kd and was not N-glycosylated. This also is consistent with the above fact indicated by Yoshida et al. (2000).

Example 12

Confirmation of the Protein Expressed from the Recombinants (The Immunoprecipitation Method)

Furthermore, the protein expressed from the recombinant virus was investigated using the immunoprecipitation method.

The CEF monolayer infected with recombinant virus was incubated with a methionine-free growth medium (0.5% FCS). Then, it was incubated in a medium in which [$^{35}$S]-Met isotope (100 mCi/ml) was added to a Met-free MEM medium (0.5%, FCS) at 37° C. for 16–48 hours. After harvesting the cells, they were solubilized by adding the lysing buffer (50 mM Tris (pH 7.5), 150 mM NaCl, 0.5% NP-40, 0.1% aprotinin). After centrifugation to remove the precipitate, anti-TTMG-1 antiserum or Mab 35A6 and Protein G-Agarose (Roche 1243233) were mixed and incubated at 4° C. The precipitate was collected by centrifugation, and washed in the washing Buffer (50 mM Tris (pH 7.5), 150 mM NaCl, 1% Triton X-100, 1% sodium deoxycholate (NaDOC), 0.1% SDS), to which the SDS Sample Buffer was added, and boiled at 100° C. for 10 min., and the supernatant was made for the sample. Each sample was subjected to SDS-PAGE, and the gel was dried and exposed to X-ray film to visualize.

Figure 5:
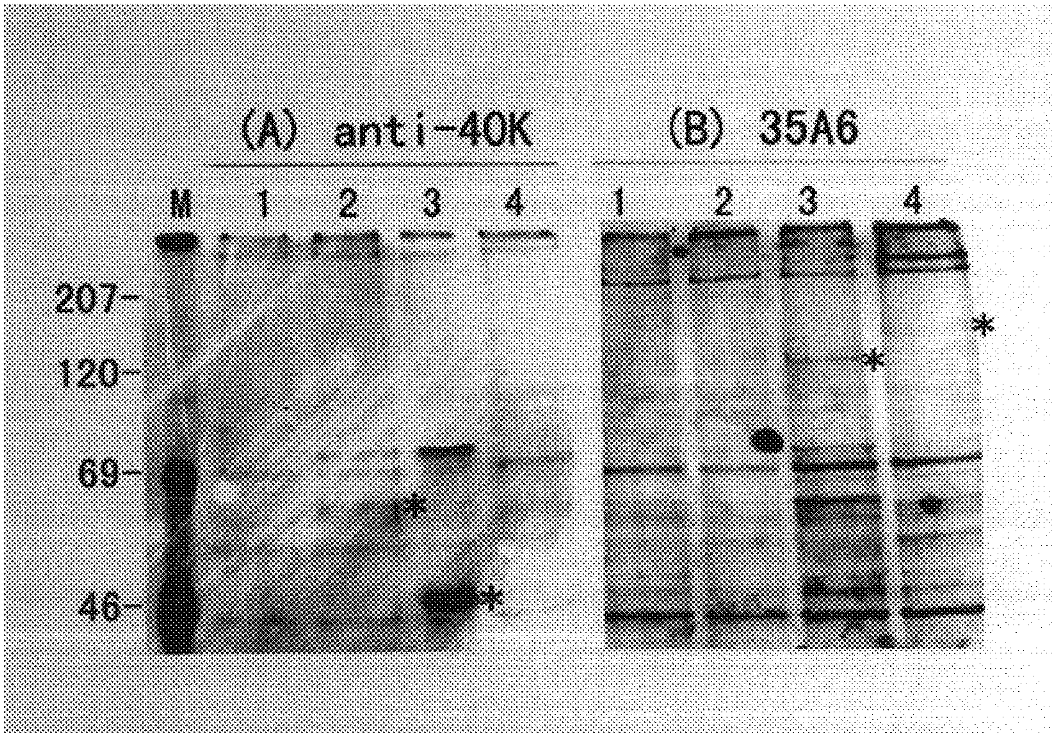
In FIG. 5, A indicates the result in which the antigen protein was detected by immunoprecipitation with anti-TTMG-1 (anti-40K) antiserum, and B indicates the result in which it was detected by immunoprecipitation with the monoclonal antibody 35A6 that reacts with the antigen protein MGC3. In both of panel A and B, lane 1 indicates the result from the virus (parent FPV) containing no antigen gene, lane 2 indicates the result from the virus containing the unmodified TTMG-1 gene that expresses the glycosylated TTMG-1 antigen, lane 3 indicates the result from the virus containing the modified TTMG-1 gene that expresses the non-N-glycosylated TTMG-1 antigen and the modified mgc3 antigen gene that expresses the non-N-glycosylated MGC3 antigen, and lane 4 indicates the result from the virus containing the unmodified mgc3 gene that expresses the N-glycosylated MGC3 antigen.

For the recombinant fowlpox virus rFPV-B/MG40/M11 (Lane 3) obtained in Example 8, immunoprecipitation was performed using anti-TTMG-1 antiserum (panel A) and Mab 35A6 (panel B) to investigate the expressed protein (FIG. 5). The expression of the TTMG-1 antigen can be confirmed in panel A, and the expression of MGC3 antigen in panel B. The recombinant fowlpox virus 40K-S (Lane 2) described in International Patent Publication WO97/36924 is a control in panel B, and the recombinant fowlpox virus recFPV-MGC3 (Lane 4) described in Yoshida et al. (2000) is a control in panel A. The parent fowlpox virus BLEN strain (Lane 1) is a control in both of panels A and B. It was confirmed, in immunoprecipitation using anti-TTMG-1 antiserum, that rFPV-B/MG40/M11 (Lane .3) having the modified TTMG-1 antigen expresses about 50 kd non-N-glycosylated TTMG-1 antigen as in the result of the Western blotting method in Example 11. On the other hand, 40K-S (Lane 2) having the unmodified TTMG-1 antigen expressed about 60 kd N-glycosylated TTMG-1 antigen. It was also confirmed, in immunoprecipitation using Mab 35A6, that rFPV-B/MG40/M11 (Lane 3) having a re-modified mgc3 gene expressed about 120 kd non-N-glycosylated MGC3 antigen as in the result of the Western blotting method in Example 11.

On the other hand, recFPV-MGC3 that expresses an unmodified MGC-3 antigen expressed an about 140 kd N-glycosylated MGC-3 antigen as in the result of the Western blotting method in Example 11.

From the foregoing, as was demonstrated in Examples 10–12, the addition of a N-linked sugar chain (N-glycosylation) can be prevented by deleting a N-glycosylation site.

Reference Example 3

Mycoplasma Challenge Test on Recombinant FPV-inoculated Chickens

The challenge test was performed according to the Japanese Standards for Biological Products of Animals. The method is briefly explained below. Using eggs of white leghorn SPF chickens (chicken species: Line-M, Nippon Institute for Biological Science), 5 weeks after hatch, recombinant FPV was inoculated by wing web stab to $10^4$ pfu per chick. The recombinant FPVs used were two: recombinant FPV described in International Patent Publication WO97/36924, 40K-S, and recFPV-MGC3-S reported by Yoshida et al. (2000). Two weeks after vaccination, chickens were challenged with the virulent MG-R strain. The challenge method was performed according to the Standards for Biological Products of Animals, and the chickens were challenged to the trachea with $4.8\times10^4$ CFU per chick. On day 14 after the challenge, the chickens were necropsied and dissected to prepare histopathological samples of the trachea, for which the tracheal lesion scores were determined based on the thickness of the mucosal tissue of the trachea and the histopathological findings. As described in International Patent Publication WO97/36924, the criteria of scoring is the same as the Japanese Standards for the Products, and the mean of the bronchial lesion scores of chickens in each group was made the score of the group. The result is shown in Table 3.

TABLE 3

Mycoplasma challenge test on recombinant FPV-inoculated chickens - 1

| | No. of chickens | tracheal lesion score |
|---|---|---|
| Challenge controls | 10 | 2.53 |
| 40K-S | 10 | 1.96 |
| recFPV-MGC3-S | 10 | 2.78 |

The result confirmed that recFPV-MGC3-S had no effect but the recombinant FPV 40K-S had a vaccine effect.

Example 13

Mycoplasma Challenge Test on Recombinant FPV-Inoculated Chickens

The challenge test was basically performed according to the USDA-9CFR. The method is briefly explained below. Using eggs of white leghorn SPF chickens (chicken species: Line-M, Nippon Institute for Biological Science), 4 weeks after hatch, recombinant FPV was inoculated by wing web stab to $10^4$ pfu per chick. The recombinant FPVs used were three: recombinant FPV described in International Patent Publication WO97/36924, 40K-S, rFPV-B/MG40-S obtained in Example 8, and rFPV-B/MG40- obtained in Example 8. As the control, the parent virus of the recombinant, the FPV BLEN strain, was also inoculated. The commercially available vaccine of *Mycoplasma gallisepticum* was inoculated as described in the directions. Three weeks after vaccination, chickens were challenged with virulent MG-R strain by spraying a bacterial solution of $1.0\times10^{10}$ CCU for 1 minute. 10 days after challenge, the chickens were necropsied, for which the tracheal lesion score was determined by the method of Evans et al. The detailed method of scoring is as follows:

Criteria of scores are as follows;

Criteria of scores are as follows;

| Score | findings |
|---|---|
| 0 | normal air sac, clear and thin |
| 1 | only cloudiness or gray areas with slight thickening or flecks of yellowish exudate, involving a very limited area of one or two air sacs |
| 2 | readily visible grayish or yellow exudate, sometimes foamy, with thickening of the air sac, involving one or portions of two air sacs |
| 3 | somewhat more severe exudative, thickened airsacculitis, but mainly more extensive, involving essentially three air-sac regions |
| 4 | severe airsacculitis with considerable exudate and thickening of almost all air-sac regions |

The score for each chicken was determined, and averaged in each group to obtain the mean score. Test of significant difference was performed between the non vaccinated challenge control group and the vaccinated group using the Mann-Whitney U-test.

TABLE 4

Mycoplasma challenge test on recombinant FPV-inoculated chickens - 2

| Virus | No. of chickens | Mean score | Significant difference |
|---|---|---|---|
| rFPV-B/MG40-S | 10 | 1.00 | * |
| rFPV-B/MG40- | 10 | 1.88 | * |
| 40K-S | 10 | 1.78 | * |
| Live Mg vaccine | 10 | 2.10 | * |
| Parent FPV | 10 | 3.38 | |
| Challenge controls | 10 | 2.90 | |

*: Significant difference with a significance level of 1%.

Based on the result, the vaccine effect was observed in all of the three recombinant FPVs, and vaccine effects were equal to or better than the live vaccine. Furthermore, it was demonstrated that, among the three, rFPV-B/MG40-S that expresses the non-N-glycosylated TTMG-1 antigen has a higher vaccine effect than rFPV-B/MG40- or 40K-S that expresses the N-glycosylated TTMG-1 antigen.

Example 14

Mycoplasma Challenge Test on Recombinant FPV-inoculated Chickens

The challenge test was performed as in Example 13, and major differences will be described. Using eggs of white leghorn SPF chickens (Line-M, Nippon Institute for Biological Science), 4 weeks after hatch, recombinant FPV was inoculated by wing web stab to $10^4$ pfu per chick. The recombinant FPV used was rFPV-B/MG40/M11. The commercially available vaccine of *Mycoplasma gallisepticum* was inoculated as described in the directions. Three weeks after vaccination, chickens were challenged with the virulent MG-R strain by spraying a bacterial solution of $1.0\times10^{10.67}$ CCU for 1 minute. Ten days after challenge, the chickens were necropsied, for which the air sac lesion score was determined by the method of Evans et al. As in Example 13, the test of significant difference was performed between the vaccinated non challenge control group and the vaccinated group using the Mann-Whitney U-test.

TABLE 5

Mycoplasma challenge test on recombinant FPV-inoculated chickens - 3

| Group | No. of chickens | Mean score | Significant difference |
|---|---|---|---|
| rFPV-B/40K/M11 | 9 | 1.67 | * |
| Live Mg vaccine | 10 | 1.90 | *2 |
| Challenge controls | 9 | 3.33 | |

*: Significant difference with a significance level of 1%

*: Significant difference with a significance level of 5%

Based on the result, rFPV-B/MG40/M11 that expresses the non-N-glycosylated TTMG-1 antigen and the MGC3 antigen exhibited a vaccine effect exceeding the live vaccine.

Example 15

Mycoplasma Challenge Test on Recombinant FPV-inoculated Chickens

The challenge test was performed as in Example 13, and major differences will be described. Using eggs of white leghorn SPF chickens (SPAFAS), 4 weeks after hatching, recombinant FPV was inoculated by wing web stab to $10^4$ $TCID_{50}$ per chick. The recombinant FPVs used were two: rFPV-B/MG40-S and rFPV-B/MG40/M11. The commercially available vaccine of *Mycoplasma gallisepticum* was inoculated as described in the directions. Three weeks after vaccination, chickens were challenged with the virulent MG-R strain by spraying a bacterial solution of $1.0 \times 10^{8.86}$ CCU for 1 minute. Ten days after challenge, the chickens were necropsied, for which the air sac lesion score was determined by the method of Evans et al. As in Example 13, the test of significant difference was performed between the vaccinated non challenge control group and the vaccinated group using the Mann-Whitney U-test.

TABLE 6

Mycoplasma challenge test on recombinant FPV-inoculated chickens - 4

| Group | No. of chickens | Mean score | Significant difference |
|---|---|---|---|
| Challenge controls | 20 | 2.15 | |
| Live Mg vaccine | 20 | 0.60 | * |
| rFPV-B/MG40-S | 20 | 1.7 | |
| rFPV-B/MG40/M11 | 20 | 1.15 | * |
| Negative controls | 10 | 0 | |

*: Significant difference with a significance level of 1%

Based on the result, the vaccine effect of two recombinants rFPV-B/MG40-S and rFPV-B/MG40/M11 that express the non-N-glycosylated TTMG-1 antigen was confirmed. Furthermore, rFPV-B/MG40/M11 that expresses the non-N-glycosylated TTMG-1 antigen and the non-N-glycosylated MGC3 antigen exhibited a vaccine effect exceeding rFPV-B/MG40-S that only expresses the non-N-glycosylated TTMG-1 antigen.

Example 16

Mycoplasma Challenge Test on Recombinant FPV-inoculated Chickens

The challenge test was performed as in Example 13, and major differences will be described. Using eggs of white leghorn SPF chickens (Line-M, Nippon Institute for Biological Science), 4 weeks after hatch, recombinant FPV was inoculated by wing web stab to $10^4$ pfu per chick. The recombinant FPVs used were three: rFPV-B/MG-1 to rFPV-B/MG-3 described in Example 8. Three weeks after vaccination, chickens were challenged with the virulent MG-R strain by spraying a bacterial solution of $1.0 \times 10^{9.85}$ CCU for 1 minute. Ten days after the challenge, the chickens were necropsied, for which the air sac lesion score was determined by the method of Evans et al. As in Example 17, the test of significant difference was performed between the vaccinated non-challenge control group and the vaccinated group using the Mann-Whitney U-test.

TABLE 7

Mycoplasma challenge test on recombinant FPV-inoculated chickens - 5

| Group | No. of chickens | Mean score | Significant difference |
|---|---|---|---|
| Challenge controls | 20 | 3.50 | |
| rFPV-B/MG-1 | 20 | 1.35 | * |

TABLE 7-continued

Mycoplasma challenge test on recombinant FPV-inoculated chickens - 5

| Group | No. of chickens | Mean score | Significant difference |
|---|---|---|---|
| rFPV-B/MG-2 | 19 | 1.74 | * |
| rFPV-B/MG-3 | 18 | 1.26 | * |
| Negative controls | 5 | 0.00 | |

*: Significant difference with a significance level of 1%

Based on the result, vaccine effect was confirmed in all of rFPV-B/MG-1 to rFPV-B/MG-3 that express the non-N-glycosylated MGC3 antigen.

Example 17

Mycoplasma Challenge Test on Recombinant FPV-inoculated Chickens

The challenge test was performed as in Example 13, and major differences will be described. Using eggs of white leghorn SPF chickens (SPAFAS), 8 weeks after hatch, recombinant FPV was inoculated by wing web stab to $10^{3.5}$ $TCID_{50}$ pfu per chick. The recombinant FPVs used were three: rFPV-B/MG-1 to rFPV-B/MG-3 obtained in Example 8. The live vaccine of *Mycoplasma gallisepticum* was inoculated as described in the directions. Three weeks after vaccination, chickens were challenged with the virulent MG-R strain by spraying a bacterial solution of $1.0 \times 10^{8.6}$ CCU for 1 minute. Ten days after challenge, the chickens were necropsied, for which the air sac lesion score was determined by the method of Evans et al. As in Example 14, the test of significant difference was performed between the vaccinated non challenge control group and the vaccinated group using the Mann-Whitney U-test.

TABLE 8

Mycoplasma challenge test on recombinant FPV-inoculated chickens - 6

| Group | No. of chickens | Mean score | Significant difference |
|---|---|---|---|
| Challenge controls | 30 | 1.78 | |
| rFPV-B/MG-1 | 30 | 0.37 | * |
| rFPV-B/MG-2 | 30 | 0.39 | * |
| rFPV-B/MG-3 | 30 | 0.56 | * |
| Live Mg vaccine | 30 | 0.43 | * |
| Negative controls | 5 | 0.00 | |

*: Significant difference with a significance level of 1%

Based on the result, vaccine effect was confirmed in all of rFPV-B/MG-1 to rFPV-B/MG-3 that express the non-N-glycosylated MGC3 antigen.

Example 18

Mycoplasma Challenge Test on Recombinant FPV- and Recombinant HVT-inoculated Chickens The challenge test was performed as in Example 13, and major differences will be described. Using eggs of white leghorn SPF chickens (Line-M, Nippon Institute for Biological Science), 3 days after hatch, recombinant HVT was subcutaneously inoculated to $3 \times 10^3$ PFU per chick, and three weeks after hatch, recombinant FPV was inoculated by wing web stab to $10^4$ $TCID_{50}$ pfu per chick. The recombinant HVTs used were rHVT/PecMG40KS and rHVT/Bac40KS-CMVM11 obtained in Example 9. The recombinant FPV used was rFPV/MG-1 obtained in Example 8. The commercially available live vaccine of *Mycoplasma gallisepticum* was inoculated three weeks after hatch as described in the directions. Seven weeks after hatching, chickens were challenged with the virulent MG-R strain by spraying a bacterial solution of $1.0\times10^{9.4}$ CCU for 1 minute. Ten days after the challenge, the chickens were necropsied, for which the air sac lesion score was determined by the method of Evans et al. As in Example 13, the test of significant difference was performed between the vaccinated non challenge control group and the vaccinated group using the Mann-Whitney U-test.

TABLE 9

Mycoplasma challenge test on recombinant FPV- and recombinant HVT-inoculated chickens

| Group | No. of chickens | Mean score | Significant difference |
|---|---|---|---|
| rFPV-B/MG-1 | 15 | 1.20 | *2 |
| rHVT/PecMG40KS | 16 | 1.50 | * |
| rHVT/Bac40KS-CMVM11 | 15 | 2.00 | |
| Live Mg vaccine | 14 | 1.79 | * |
| Challenge controls | 12 | 2.75 | |

*: Significant difference with a significance level of 1%
*2: Significant difference with a significance level of 5%

Based on the result, vaccine effect was confirmed in the recombinant HVT of the present invention, rHVT/PecMG40KS, that expresses the non-N-glycosylated TTMG-1 antigen and rFPV-B/MG-1 that expresses the non-N-glycosylated MGC3 antigen. Furthermore, the vaccine effect of rHVT/Bac40KS-MVM11 that expresses the non-N-glycosylated TTMG-1 antigen and the non-N-glycosylated MGC3 antigen was confirmed.

Example 19

Mycoplasma Challenge Test on Recombinant HVT-inoculated Chickens

The challenge test was performed as in Example 13, and major differences will be described. Using eggs of white leghorn SPF chickens (Line-M, Nippon Institute for Biological Science), on the day of hatch, recombinant FPV was subcutaneously inoculated to $10^3$ or $10^4$ $TCID_{50}$ per chick. The recombinant HVT used was rHVT/PecMG40KS constructed in Example 9. The commercially available *Mycoplasma gallisepticum* live vaccine was inoculated three weeks after hatch as described in the directions. Seven weeks after hatch, a MG virulent R strain was challenged by spraying a bacterial solution of $1.0\times10^{5.59}$ CCU for 1 minute. Ten days after the challenge, the chickens were necropsied, for which the air sac lesion score was determined by the method of Evans et al. As in Example 13, the test of significant difference was performed between the vaccinated non challenge control group and the vaccinated group using the Mann-Whitney U-test.

TABLE 10

Mycoplasma challenge test on recombinant HVT-inoculated chicken

| Group | Dose $\log_{10}$/chick | No. of chickens | Mean score | Significant difference |
|---|---|---|---|---|
| rHVT/PecMG40KS | 4.0 | 8 | 2.00 | * |
| rHVT/PecMG40KS | 3.0 | 7 | 2.57 | * |
| Live Mg vaccine label | | 10 | 2.10 | * |
| Challenge controls | | 12 | 3.50 | |
| Negative controls | | 5 | 0.00 | |

*: Significant difference with a significance level of 1%

Based on the result, vaccine effect was confirmed in rHVT/PecMG40KS, a recombinant HVT that expresses the non-N-glycosylated TTMG-1 antigen.

REFERENCE CITED

U.S. Patent Documents

U.S. Pat. No. 5,180,675 January/1993 Drillien et al. 435/235.1
U.S. Pat. No. 5,387,519 February/1995 Yanagida et al. 435/235.1
U.S. Pat. No. 5,489,430 February/1996 Saito et al. 424/190.1
U.S. Pat. No. 5,766,594 June/1998 Kodama et al. 424/190.1
U.S. Pat. No. 5,871,742 February/1999 Saitoh et al. 424/199.1

Foreign Patent Documents

WO97/24370 July/1997 WIPO
WO97/36924 October/1997 WIPO
WO99/18215 April/1999 WIPO
2766984 April/1998 Japan.
2001-188 January/2001 Japan.

Other Publications

Andre, S. et al., "Increased immune response elicited by DNA vaccination with a synthetic gp120 sequence with optimized codon usage." J. Virol. 72:1497–1503, 1998.

Davison, A. J. and J. B Moss. "Structure of vaccinia virus early promoters." J. Mol. Biol. 210:749–769, 1989.

Davison, A. J. and B. Moss. "Structure of vaccinia virus late promoters." J. Mol. Biol. 210:771–784, 1989.

Greuel, B. T. et al., "Transcriptional activity of the Rous sarcoma virus long terminal repeat correlates with binding of a factor to an upstream CCAAT box in vitro." Virology 177:33–43, 1990.

Gunning, P. et al., "A human beta-actin expression vector system directs high-level accumulation of antisense transcripts." Proc. Natl. Acad. Sci. U.S.A. 84:4831–4835, 1987.

Kost, T. A. et al., "The nucleotide sequence of the chick cytoplasmic beta-actin gene." Nucleic Acids. Res. 11:8287–8301, 1983.

Morgan, R. W. et al., "Transfection of chicken embryo fibroblasts with Marek's disease virus DNA." Avian Dis. 34:345–351, 1990.

Nakamura Y. et al., "Condon usage tabulated from the international DNA sequence database." Nucleic Acids. Res. 24:214–215, 1996.

Ross L. et al., 16th International Herpes Workshop (1991)

Ross, L. J. N et al., "Construction and properties of a turkey herpesvirus recombinant expressing the Marek's disease virus homologue of glycoprotein B of herpes simplex virus." J. Gen. Virol 74:371–377, 1993.

Sakaguchi, M. et al., "Construction of recombinant Marek's disease virus type I (MDV1) expressing the *Escherichia coli* lacZ gene as a possible live vaccine vector: the US10 gene of MDVI as a stable insertion site." Vaccine 12:953–957, 1994.

Sondermeijer, P. J. et al., "Avian herpesvirus as a live viral vector for the expression of heterologous antigens." Vaccine 11:349–358, 1993.

Stinski, M. F. and T. J. Roehr. "Activation of the major immediate early gene of human cytomegalovirus by cis-acting elements in the promoter-regulatory sequence and by virus-specific trans-acting components." J. Virol. 55:431–441, 1985.

Yanagida N et al., "Recombinant fowlpox viruses expressing the glycoprotein B homolog and the pp38 gene of Marek's disease virus. " Journal of Virology 66:1402–1408, 1992.

Yanagida, N. et al., "Nucleotide and predicted amino acid sequences of Marek's disease virus homologues of herpes simplex virus major tegument proteins." J. Gen. Virol. 74:1837–1845, 1993.

Yoshida, S. et al., "Identification and expression of a *Mycoplasma gallisepticum* surface antigen recognized by a monoclonal antibody capable of inhibiting both growth and metabolism" Infect. Immun., vol. 68, pp. 3186–3192, 2000.

Weir, J. P. and B. Moss. "Regulation of expression and nucleotide sequence of. a late vaccinia virus gene." J. Virol. 51:662–669, 1984.

What is claimed is:

1. An isolated DNA molecule, whose sequence comprises:

a portion of the genome of a prokaryotic cell, encoding an antigen, in which at least one DNA region encoding an NXB site, wherein N is asparagine, X is any amino acid other than proline, and B is serine or threonine, has been altered so that no N-glycosylation occurs at said NXB site during expression of the DNA molecule in a eukaryotic cell, wherein said prokaryotic cell is Mycoplasma.

2. An isolated DNA molecule, whose sequence comprises:

a portion of the genome of a prokaryotic cell, encoding an antigen, in which at least one DNA region encoding an NXB site, wherein N is asparagine, X is any amino acid other than proline, and B is serine or threonine, has been altered so that no N-glycosylation occurs at said NXB site during expression of the DNA molecule in a eukaryotic cell, wherein said prokaryotic cell is a Mycoplasma, and said portion of the genome includes the DNA sequence according to SEQ ID NO: 1 or SEQ ID NO: 2.

3. A fused DNA molecule, wherein a DNA encoding a signal sequence has been ligated to the N-terminal end of a DNA molecule, wherein the sequence of said DNA molecule comprises a portion of the genome of a prokaiyotic cell encoding an antigen, in which at least one DNA region encoding an NXB site, wherein N is asparagine, X is any amino acid other than proline, and B is serine or threonine, has been altered so that no N-glycosylation occurs at said NXB site during expression of the DNA molecule in a eukaryotic cell so that the fused DNA molecule may be expressed as a fusion protein, wherein said portion of the genome of a prokaryotic cell has a DNA sequence described in SEQ ID NO: 1 or 2, and said signal sequence is a signal sequence from the gB of Marek's disease virus or a signal sequence from the gG of Rabies virus.

4. A recombinant virus that has integrated therein (1) a DNA molecule whose sequence comprises a portion of the genome of a prokaryotic cell encoding an antigen, wherein said prokaryotic cell is Mycoplasma. in which at least one DNA region encoding an NXB site, wherein N is asparagine, X is any amino acid other than proline, and B is serine or threonine, has been altered so that no N-glycosylation occurs at said NXB site during the expression of the DNA molecule in a eukaryotic cell, or (2) a fused DNA molecule in which a DNA encoding a signal sequence is ligated to the N-terminal end of said DNA molecule of (1) so that it may be expressed as a fusion protein.

5. The recombinant virus according to claim 4, wherein the alteration that prevents N-glycosylation is at least one of the following:

(1) the alteration of the DNA sequence encoding asparagine (N) to a DNA sequence encoding an amino acid other than asparagine;

(2) the alteration of the DNA sequence encoding any amino acid (X) other than proline to a DNA sequence encoding proline, and (3) the alteration of the DNA sequence encoding serine or threonine (B) to a DNA sequence encoding an amino acid other than serine or threonine.

6. A recombinant virus that has integrated therein (1) a DNA molecule whose sequence comprises a portion of the genome of a prokaryotic cell, wherein said prokaryotic cell is Mycoplasma, in which at least one DNA region encoding NXB, wherein N is asparagine, X is any amino acid other than proline, and B is serine or threonine, has been altered so that no N-glycosylation occurs during the expression of the DNA molecule in a eukaryotic cell, or (2) a fused DNA molecule in which a DNA encoding a signal sequence is ligated to the N-terminal end of said DNA molecule of (1) so that it may be expressed as a fusion protein, wherein said prokaryotic cell is a Mycoplasma, and said portion of the genome includes the DNA sequence according to SEQ ID NO: 1 or SEQ ID NO: 2.

7. A recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA region encoding NXB, wherein N is asparagine, X is any amino acid other than proline, and B is serine or threonine, has been altered so that no N-glycosylation occurs at said NXB site during the expression of said fused DNA molecule in a eukaryotic cell, so that it may be expressed as a fusion protein.

8. A recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA regions encoding NXB, wherein N is asparagine, X is any amino acid other than proline, and B is seine or threonine, has been altered so that no N-glycosylation occurs at said NXB site during the expression of said fused DNA molecule in a eukaryotic cell, so that it may be expressed as a fusion protein, wherein said signal sequence is a signal sequence from the gB gene of Marek's disease virus or a signal sequence from the gG gene of Rabies virus.

9. A recombinant virus that has integrated therein (1) a DNA molecule whose sequence comprises a portion of the genome of a prokaryotic cell encoding an antigen, wherein said prokaryotic cell is Mycoplasma, in which at least one DNA region encoding NXB, wherein N is asparagine, X is any amino acid other than proline, and B is serine or threonine, has been altered so that no N-glycosylation occurs during the expression of the DNA molecule in a eukaryotic cell, or (2) a fused DNA molecule in which a DNA encoding a signal sequence is ligated to the N-terminal end of said DNA molecule of(l) so that it may be expressed as a fusion protein, or a recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA regions encoding NXB, wherein N is asparagine, X is any amino acid other than proline, and B is serine or threonine, has been altered so that no N-glycosylation occurs at said NXB site during the expression of said %sed DNA molecule in a eukaryotic cell, so that it may be expressed as a fusion protein, wherein said virus is a poxyirus or a herpesvirus.

10. A recombinant virus that has integrated therein (1) a DNA molecule whose sequence comprises a portion of the genome of a prokaryotic cell encoding an antigen, wherein said prokaryotic cell is Mycoplasma, in which at least one DNA region encoding NXB, wherein N is asparagine, X is any amino acid other than proline, and B is serine or threonine, has been altered so that no N-glycosylation occurs during the expression of the DNA molecule in a eukaryotic cell, or (2) a fused DNA molecule in which a DNA encoding a signal sequence is ligated to the N-terminal end of said DNA molecule of(l) so that it may be expressed as a fusion protein, or a recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA regions encoding NXB, wherein N is asparagine, X is any amino acid other than proline, and B is serine or threonine, has been altered so that no N-glycosylation occurs at said NXB site during the expression of said fused DNA molecule in a eukaryotic cell, so that it may be expressed as a fusion protein, wherein said virus is a virus that infects avians.

11. A recombinant virus that has integrated therein (1) a DNA molecule whose sequence comprises a portion of the genome of a prokaryotic cell encoding an antigen, wherein said prokaiyotic cell is Mycoplasma, in which at least one DNA region encoding NXB, wherein N is asparagine, X is any amino acid other than proline, and B is serine or threonine, has been altered so that no N-glycosylation occurs during the expression of the DNA molecule in a eukaryotic cell, or (2) a fused DNA molecule in which a DNA encoding a signal sequence is ligated to the N-terminal end of said DNA molecule of (1) so that it may be expressed as a fusion protein, or a recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA regions encoding NXB, wherein N is asparagine, X is any amino acid other than proline, and B is serine or threonine, has been altered so that no N-glycosylation occurs at said NXB site during the expression of said fused DNA molecule in a eukaryotic cell, so that it may be expressed as a fusion protein, wherein said virus is an avipoxvirus.

12. A recombinant virus that has integrated therein (1) a DNA molecule whose sequence comprises a portion of the genome of a prokaryotic cell encoding an antigen, wherein said prokaryotic cell is Mycoplasma, in which at least one DNA region encoding NXB, wherein N is asparagine, X is any amino acid other than proline, and B is serine or threonine, has been altered so that no N-glycosylation occurs during the expression of the DNA molecule in a eukaryotic cell, or (2) a fused DNA molecule in which a DNA encoding a signal sequence is ligated to the N-terminal end of said DNA molecule of(l) so that it may be expressed as a fusion protein, or a recombinant virus that has integrated therein a fused DNA molecule, wherein a first DNA encoding a signal sequence that has been altered so that no N-glycosylation occurs in the protein encoded by said first DNA during the expression in a eukaryotic cell has been ligated to the N-terminal end of a second DNA molecule comprising a portion of the genome of a prokaryotic cell encoding an antigen, wherein said prokaryotic cell is Mycoplasma, in which at least one DNA regions encoding NXB, wherein N is asparagine, X is any amino acid other than proline, and B is serine or threonine, has been altered so that no N-glycosylation occurs at said NXB site during the expression of said fused DNA molecule in a eukaryotic cell, so that it may be expressed as a fusion protein, wherein said virus is a Marek's disease virus type I, type II, or type III.

13. A vaccine comprising the recombinant virus according to claim 4 or 7.

* * * * *